(12) United States Patent
Garrett et al.

(10) Patent No.: US 10,584,812 B2
(45) Date of Patent: *Mar. 10, 2020

(54) STRETCH HOSE AND HOSE PRODUCTION METHOD

(71) Applicant: GLOBALMED, INC., Trenton (CA)

(72) Inventors: Carl J Garrett, Beverly, MA (US); Ralf Jourdan, Moerfelden-Walldorf (DE)

(73) Assignee: GLOBALMED, INC., Trenton, Ontario (CA)

( * ) Notice: Subject to any disclaimer, the term of this patent is extended or adjusted under 35 U.S.C. 154(b) by 178 days.

This patent is subject to a terminal disclaimer.

(21) Appl. No.: 15/932,864

(22) Filed: May 9, 2018

(65) Prior Publication Data

US 2018/0266592 A1  Sep. 20, 2018

Related U.S. Application Data

(60) Continuation of application No. 15/530,530, filed on Jan. 25, 2017, now Pat. No. 9,989,174, which is a
(Continued)

(51) Int. Cl.
*F16L 11/24* (2006.01)
*B29C 48/12* (2019.01)
(Continued)

(52) U.S. Cl.
CPC ............. *F16L 11/24* (2013.01); *A47L 9/248* (2013.01); *B29C 48/12* (2019.02); *B29C 48/131* (2019.02);
(Continued)

(58) Field of Classification Search
CPC .......... A61M 16/08; F16L 11/04; F16L 11/08; F16L 11/081; F16L 11/082; F16L 11/083;
(Continued)

(56) References Cited

U.S. PATENT DOCUMENTS

| 511,188 A | 12/1893 | Barnard | 439/192 |
| 1,397,682 A | 11/1921 | Geier et al. | 174/46 |

(Continued)

FOREIGN PATENT DOCUMENTS

| DE | 3312434 A1 | 3/1983 | A47L 9/28 |
| DE | 3835248 A1 | 10/1988 | B29C 55/10 |

(Continued)

*Primary Examiner* — Carson Gross
(74) *Attorney, Agent, or Firm* — David A. Burge

(57) ABSTRACT

A method of continuously forming an axially extensible and retractable hose comprising: continuously forming an axially extending helix with axially spaced reinforcing coils from extruded thermoplastic material having a uniform cross-section along its length; and continuously bridging between an adjacent pair of the reinforcing coils with a continuous web of extruded thermoplastic material of substantially uniform width and relatively thin cross-section to form a continuous, helically extending sidewall, with the web having one of two opposite edge regions bonded continuously to a relatively flat outer bonding surface of a radially outwardly located portion of one of the adjacent pair of reinforcing coils, with the web having the other of the edge regions bonded continuously to a relatively flat inner bonding surface of a radially inwardly located portion of the other of the pair of reinforcing coils, and with the edge regions continuously radially separated from each other by the helix.

22 Claims, 7 Drawing Sheets

Related U.S. Application Data division of application No. 14/544,767, filed on Feb. 16, 2015, now Pat. No. 9,556,978, which is a continuation-in-part of application No. 13/986,465, filed on May 6, 2013, now Pat. No. 9,308,698, which is a continuation of application No. 12/799,263, filed on Apr. 21, 2010, now Pat. No. 8,453,681, which is a continuation-in-part of application No. 12/354,291, filed on Jan. 15, 2009, now abandoned, said application No. 14/544,767 is a continuation-in-part of application No. 13/507,172, filed on Jun. 11, 2012, now Pat. No. 9,505,164.

(60) Provisional application No. 61/627,425, filed on Oct. 12, 2011, provisional application No. 61/335,023, filed on Dec. 30, 2009, provisional application No. 61/966,171, filed on Feb. 18, 2014.

(51) Int. Cl.

| | | |
|---|---|---|
| *B29C 48/03* | (2019.01) | |
| *B29C 48/154* | (2019.01) | |
| *F16L 11/112* | (2006.01) | |
| *A47L 9/24* | (2006.01) | |
| *B29C 53/58* | (2006.01) | |
| *B29C 53/82* | (2006.01) | |
| *B29D 23/18* | (2006.01) | |
| *B32B 37/14* | (2006.01) | |
| *B32B 37/15* | (2006.01) | |
| *F16L 11/115* | (2006.01) | |
| *A61M 16/08* | (2006.01) | |
| *B29L 23/00* | (2006.01) | |
| *B29L 23/18* | (2006.01) | |

(52) U.S. Cl.
CPC .......... *B29C 48/154* (2019.02); *B29C 53/581* (2013.01); *B29C 53/825* (2013.01); *B29D 23/18* (2013.01); *B32B 37/142* (2013.01); *B32B 37/15* (2013.01); *F16L 11/112* (2013.01); *F16L 11/115* (2013.01); *A61M 16/08* (2013.01); *B29C 53/582* (2013.01); *B29L 2023/005* (2013.01); *B29L 2023/18* (2013.01); *B32B 2307/546* (2013.01); *B32B 2597/00* (2013.01)

(58) Field of Classification Search
CPC .......... F16L 11/10; F16L 11/11; F16L 11/112; F16L 11/115; B29D 23/18; B29L 2023/18; B29C 53/582; B29C 53/58; B29C 53/581; B29C 53/583; B29C 53/584; B29C 53/585; B29C 53/586; B29C 53/587; B29C 53/60
See application file for complete search history.

(56) References Cited

U.S. PATENT DOCUMENTS

| | | | |
|---|---|---|---|
| 1,474,528 A | 11/1923 | Hurst | 219/208 |
| 1,995,302 A | 3/1935 | Goldstein | 128/254 |
| 2,073,335 A | 3/1937 | Connell | 138/49 |
| 2,330,651 A | 9/1943 | Welger | 138/56 |
| 2,396,059 A | 3/1946 | Roberts | 138/56 |
| 2,398,876 A | 4/1946 | Bailey | 156/194 |
| 2,430,081 A | 11/1947 | Roberts et al. | 156/144 |
| 2,486,387 A | 11/1949 | Bringolf | 138/122 |
| 2,508,774 A | 5/1950 | Roberts | 138/56 |
| 2,516,864 A | 9/1950 | Gilmore et al. | 154/8 |
| 2,560,369 A | 7/1951 | Roberts | 154/8 |
| 2,625,979 A | 1/1953 | Harris et al. | 154/6 |
| 2,634,311 A | 4/1953 | Darling | 173/326 |
| 2,641,302 A | 6/1953 | Martin et al. | 154/8 |
| 2,661,025 A | 12/1953 | Brace | 138/56 |
| 2,713,381 A | 7/1955 | Seck | 154/8 |
| 2,731,040 A | 1/1956 | Warburton | 138/49 |
| 2,731,070 A | 1/1956 | Meissner | B29C 53/785 138/132 |
| 2,734,616 A | 3/1956 | Duff | 138/122 |
| 2,739,616 A | 3/1956 | Duff | 138/56 |
| 2,740,427 A | 4/1956 | Swan | 138/122 |
| 2,745,074 A | 5/1956 | Darling | 339/16 |
| 2,793,280 A | 5/1957 | Harvey | 219/39 |
| 2,819,400 A | 10/1957 | Hewitt | 138/56 |
| 2,874,723 A | 2/1959 | Kahn | 138/56 |
| 2,895,001 A | 7/1959 | Noyes et al. | 174/47 |
| 2,901,024 A | 8/1959 | Marsden, Jr. | 154/8 |
| 2,913,011 A | 11/1959 | Noyes et al. | 138/56 |
| 2,914,790 A | 12/1959 | Warburton | 15/327 |
| 2,917,568 A | 12/1959 | Moorman et al. | 174/47 |
| 2,936,812 A | 5/1960 | Roberts | 154/7 |
| 2,940,126 A | 6/1960 | Sheridan | 18/55 |
| 2,954,802 A | 10/1960 | Duff | 138/56 |
| 2,961,007 A | 11/1960 | Martin | 138/56 |
| 2,963,750 A | 12/1960 | Pavlic | 18/59 |
| 2,994,104 A | 8/1961 | Mittag | 18/12 |
| 2,998,474 A | 8/1961 | Pavlic | 174/47 |
| 3,034,088 A | 5/1962 | Pauler et al. | 339/16 |
| 3,047,026 A | 7/1962 | Kahn | 138/122 |
| 3,058,493 A | 10/1962 | Muller | 138/122 |
| 3,076,737 A | 2/1963 | Roberts | 156/48 |
| 3,080,891 A | 3/1963 | Duff | 138/122 |
| 3,082,394 A | 3/1963 | Hahn et al. | 339/16 |
| 3,112,771 A | 12/1963 | Bringolf | 138/129 |
| 3,114,172 A | 12/1963 | Coste | 18/19 |
| 3,122,171 A | 2/1964 | Britton et al. | 138/129 |
| 3,127,227 A | 3/1964 | Edwards | 339/15 |
| 3,138,511 A | 6/1964 | Cadwallader | 156/431 |
| 3,152,202 A | 10/1964 | Murphy, Jr. | 264/167 |
| 3,155,559 A | 11/1964 | Hall | 156/195 |
| 3,157,543 A | 11/1964 | Roberts et al. | 156/143 |
| 3,163,707 A | 12/1964 | Darling | 174/47 |
| 3,169,552 A | 2/1965 | Fawick | 138/133 |
| 3,173,822 A | 3/1965 | Rigaut | 156/429 |
| 3,184,793 A | 5/1965 | Plourde | 18/14 |
| 3,188,690 A | 6/1965 | Zieg | 18/14 |
| 3,189,053 A | 6/1965 | Parr | 138/133 |
| 3,199,541 A | 8/1965 | Richitelli | 138/129 |
| 3,211,823 A | 10/1965 | Brown et al. | 174/47 |
| 3,216,458 A | 11/1965 | Sabe | 138/122 |
| 3,243,328 A | 3/1966 | Britton et al. | 156/195 |
| 3,248,272 A | 4/1966 | Sawada | 156/143 |
| 3,255,780 A | 6/1966 | Squirrell | 138/122 |
| 3,271,064 A | 9/1966 | Hall | 264/93 |
| 3,272,678 A | 9/1966 | Swan | 156/429 |
| 3,273,600 A | 9/1966 | Swan | 138/122 |
| 3,280,430 A | 10/1966 | Antrobus | 18/14 |
| 3,286,305 A | 11/1966 | Seckel | 18/19 |
| 3,297,122 A | 1/1967 | Beck | 138/122 |
| 3,300,571 A | 1/1967 | Downey et al. | 174/47 |
| 3,301,734 A | 1/1967 | Britton et al. | 156/425 |
| 3,314,039 A | 4/1967 | Opper | 339/15 |
| 3,336,172 A | 8/1967 | Hall et al. | 156/143 |
| 3,339,168 A | 8/1967 | Belicka et al. | 339/5 |
| 3,349,806 A | 10/1967 | Roberts | 138/122 |
| 3,378,673 A | 4/1968 | Hopper | 319/301 |
| 3,486,532 A | 12/1969 | Sawada | A47L 9/24 138/122 |
| 3,530,536 A | 9/1970 | Thorman et al. | B29D 23/04 18/14 |
| 3,536,559 A | 10/1970 | Pelley et al. | B65H 81/00 156/429 |
| 3,564,087 A | 2/1971 | Ruekberg | B29C 17/07 264/89 |
| 3,567,101 A | 3/1971 | Ranne | B23K 1/20 228/15 |
| 3,582,968 A | 6/1971 | Buiting et al. | H05B 3/40 219/300 |
| 3,585,361 A | 6/1971 | Rosen et al. | F27B 11/06 219/421 |

(56) References Cited

U.S. PATENT DOCUMENTS

| | | | |
|---|---|---|---|
| 3,603,403 A | 9/1971 | Horwimski | A62C 35/00 169/5 |
| 3,635,255 A | 1/1972 | Kramer | F16L 11/06 138/122 |
| 3,636,285 A | 1/1972 | Wickham et al. | H01R 33/30 200/51 |
| 3,640,312 A | 2/1972 | Bauman et al. | A47L 9/24 138/121 |
| 3,674,056 A | 7/1972 | D'Aprile | F16L 11/16 138/134 |
| 3,677,676 A | 7/1972 | Hegler | B29D 23/04 425/109 |
| 3,679,531 A | 7/1972 | Wienand et al. | A44B 21/00 161/48 |
| 3,706,624 A | 12/1972 | Rinker | B29D 17/00 156/432 |
| 3,739,815 A | 6/1973 | Rejeski | F16L 11/06 138/122 |
| 3,743,456 A | 7/1973 | Cini | B29D 23/04 425/112 |
| 3,751,541 A | 9/1973 | Hegler | B29C 17/07 264/90 |
| 3,847,001 A | 11/1974 | Thamasett | 72/96 |
| 3,856,051 A | 12/1974 | Bain | F16L 11/12 138/114 |
| 3,858,615 A | 1/1975 | Weigl | F16L 11/06 138/121 |
| 3,861,424 A | 1/1975 | Mizutani | F16L 11/08 138/119 |
| 3,886,029 A | 5/1975 | Poulsen | B65H 81/00 156/429 |
| 3,889,716 A | 6/1975 | Linhart | F16L 11/00 138/129 |
| 3,890,181 A | 6/1975 | Stent et al. | B31C 3/00 156/143 |
| 3,910,808 A | 10/1975 | Steward | B29D 23/04 156/143 |
| 3,912,795 A | 10/1975 | Jackson | A61M 15/00 261/36 |
| 3,916,953 A | 11/1975 | Nagayoshi et al. | F16L 11/08 138/129 |
| 3,919,367 A | 11/1975 | Maroschak | B29C 5/06 264/40 |
| 3,928,715 A | 12/1975 | Holden | F16L 11/12 174/47 |
| 3,962,019 A | 6/1976 | Rejeski | B65H 81/00 156/428 |
| 3,963,856 A | 6/1976 | Carlson et al. | F16L 11/12 174/47 |
| 3,964,476 A | 6/1976 | Palleni | A61M 16/00 128/145.6 |
| 3,965,526 A | 6/1976 | Doubleday | A47L 5/00 15/377 |
| 3,966,525 A | 6/1976 | Steward | B65H 81/00 156/195 |
| 4,007,737 A | 2/1977 | Paluch | A61M 17/00 128/188 |
| 4,010,054 A | 3/1977 | Bradt | B65H 81/00 156/173 |
| 4,010,748 A | 3/1977 | Dobritz | A61M 16/00 128/192 |
| 4,012,272 A | 3/1977 | Tiner | B65H 81/04 156/429 |
| 4,013,122 A | 3/1977 | Long | F28D 7/10 165/154 |
| 4,038,519 A | 7/1977 | Foucras | H05B 3/58 219/301 |
| 4,043,856 A | 8/1977 | Steward | B31C 1/00 156/195 |
| 4,048,993 A | 9/1977 | Dobritz | A61M 16/00 128/212 |
| 4,063,790 A | 12/1977 | Kleykamp et al. | H01R 3/04 339/16 |
| 4,063,988 A | 12/1977 | Choiniere et al. | B65H 81/00 156/429 |
| 4,098,298 A | 7/1978 | Vohrer | F16L 11/08 138/122 |
| 4,104,097 A | 8/1978 | Gregory et al. | B31C 1/00 156/143 |
| 4,121,624 A | 10/1978 | Chen | F16L 11/11 138/122 |
| 4,140,154 A | 2/1979 | Kanao | F16L 11/08 138/132 |
| 4,162,370 A | 7/1979 | Dunn et al. | A47L 9/24 174/47 |
| 4,167,645 A | 9/1979 | Carey | F16L 11/12 174/47 |
| 4,172,474 A | 10/1979 | Stahl | F16L 11/08 138/132 |
| 4,186,778 A | 2/1980 | Carey | F16L 11/12 138/103 |
| 4,194,081 A | 3/1980 | Medford et al. | F16L 11/11 174/47 |
| 4,196,031 A | 4/1980 | Lalikos et al. | B32B 1/08 156/143 |
| 4,203,476 A | 5/1980 | Vitellaro | F16L 11/08 138/122 |
| 4,211,457 A | 7/1980 | Meadows | H01R 3/04 339/15 |
| 4,213,811 A | 7/1980 | Hall et al. | B65H 8/00 156/195 |
| 4,224,463 A | 9/1980 | Koerber et al. | A47L 9/24 174/47 |
| 4,224,965 A | 9/1980 | Suchor | F16L 11/04 138/154 |
| 4,229,613 A | 10/1980 | Braun | F16L 11/12 174/47 |
| 4,232,667 A | 11/1980 | Chalon et al. | A61M 16/00 128/203.26 |
| 4,233,097 A | 11/1980 | Stahl | B31C 13/00 156/143 |
| 4,265,235 A | 5/1981 | Fukunaga | A61M 16/00 128/200.24 |
| 4,277,640 A | 7/1981 | Kutnyak et al. | A47L 9/24 174/47 |
| 4,294,636 A | 10/1981 | Vitellaro | B65H 81/00 156/143 |
| 4,304,266 A | 12/1981 | Kutnyak et al. | F16L 11/08 138/129 |
| 4,327,718 A | 5/1982 | Croneberg | A61M 16/00 128/205.12 |
| 4,336,798 A | 6/1982 | Beran | A61M 16/00 128/200.14 |
| 4,337,800 A | 7/1982 | Carlson et al. | F16L 11/11 138/122 |
| 4,342,612 A | 8/1982 | Lalikos et al. | F16L 11/11 138/122 |
| 4,343,672 A | 8/1982 | Kanao | B31C 1/00 156/428 |
| 4,345,805 A | 8/1982 | Finley et al. | H01R 3/04 339/16 |
| 4,350,547 A | 9/1982 | Kanao | B29D 23/12 156/143 |
| 4,354,051 A | 10/1982 | Kutnyak | A47L 9/24 174/47 |
| 4,375,381 A | 3/1983 | Carlson et al. | B65H 81/00 156/195 |
| 4,383,555 A | 5/1983 | Finley | F16L 11/08 138/129 |
| 4,394,057 A | 7/1983 | Williams et al. | H01R 38/00 339/15 |
| 4,422,702 A | 12/1983 | Nordeen | H01R 4/64 339/18 |
| 4,423,311 A | 12/1983 | Varney, Sr. | H05B 3/56 219/306 |
| 4,456,034 A | 6/1984 | Bixby | F16L 55/00 138/122 |

(56) References Cited

U.S. PATENT DOCUMENTS

| | | | |
|---|---|---|---|
| 4,459,168 A | 7/1984 | Anselm | B65H 81/00 156/143 |
| 4,462,397 A | 7/1984 | Suzuki | A61M 16/00 128/200.14 |
| 4,471,813 A | 9/1984 | Cothran | F16L 11/04 138/122 |
| 4,489,759 A | 12/1984 | Yamamura | F16L 11/00 138/122 |
| 4,490,200 A | 12/1984 | Dillon | F16L 11/11 156/143 |
| 4,490,575 A | 12/1984 | Kutnyak | A47L 9/24 174/47 |
| 4,501,948 A | 2/1985 | Yampolsky et al. | B23K 27/00 219/121 |
| 4,521,270 A | 6/1985 | Lupke | B29D 23/04 156/429 |
| 4,542,280 A | 9/1985 | Werner | F16L 11/00 138/131 |
| 4,543,951 A | 10/1985 | Phue | A61M 16/00 128/204.25 |
| 4,547,029 A | 10/1985 | Kutnyak et al. | H01R 11/08 339/16 |
| 4,553,023 A | 11/1985 | Jameson et al. | H05B 3/58 219/301 |
| 4,575,400 A | 3/1986 | Ueda et al. | B65H 81/00 156/428 |
| 4,587,145 A | 5/1986 | Kanao | F16L 11/08 428/36 |
| 4,599,784 A | 7/1986 | Canu, Jr. et al. | B23P 11/02 29/450 |
| 4,613,389 A | 9/1986 | Tanaka | F16L 11/08 156/143 |
| 4,616,894 A | 10/1986 | Baker | H01R 4/64 339/15 |
| 4,618,195 A | 10/1986 | Keane | H01R 13/73 339/16 |
| 4,621,632 A | 11/1986 | Bartels et al. | A61M 16/00 128/203.27 |
| 4,629,590 A | 12/1986 | Bagwell | B01F 3/04 261/78.2 |
| 4,637,384 A | 1/1987 | Schroeder | A61M 16/00 128/204.18 |
| 4,639,055 A | 1/1987 | Keane | H01R 3/00 339/16 |
| 4,652,063 A | 3/1987 | Genoa et al. | H01R 4/64 339/15 |
| 4,667,084 A | 5/1987 | Regge | H05B 3/58 219/301 |
| 4,686,354 A | 8/1987 | Makin | A61M 16/16 219/301 |
| 4,693,324 A | 9/1987 | Choiniere et al. | A47L 9/24 174/47 |
| 4,708,831 A | 11/1987 | Elsworth et al. | A61M 16/16 361/130 |
| 4,714,508 A | 12/1987 | Chivens et al. | B23K 27/00 156/195 |
| 4,722,334 A | 2/1988 | Blackmer et al. | A61M 16/00 |
| 4,773,410 A | 9/1988 | Blackmer et al. | A61M 16/00 128/203.26 |
| 4,780,261 A | 10/1988 | Vajtay | B29C 53/00 264/285 |
| 4,787,117 A | 11/1988 | Westergren | A47L 9/24 15/339 |
| 4,826,423 A | 5/1989 | Kemp et al. | B29C 47/06 425/505 |
| 4,829,998 A | 5/1989 | Jackson | A61M 15/00 128/203.12 |
| 4,838,258 A | 6/1989 | Dryden et al. | A61M 16/00 128/204.18 |
| 4,867,671 A | 9/1989 | Nagayoshi et al. | B29C 47/08 425/391 |
| 4,917,539 A | 4/1990 | de la Salle | F16L 1/00 405/154 |
| 4,941,469 A | 7/1990 | Adahan | A61M 16/16 128/205.18 |
| 4,955,372 A | 9/1990 | Blackmer et al. | A61M 15/00 128/203.16 |
| 4,967,744 A | 11/1990 | Chua | A61M 16/01 128/204.18 |
| 4,969,837 A | 11/1990 | Genos et al. | H01R 4/64 439/191 |
| 5,031,612 A | 7/1991 | Clementi | A61M 16/16 128/204.14 |
| 5,101,820 A | 4/1992 | Christopher | A61M 16/00 128/204.18 |
| 5,121,746 A | 6/1992 | Sikora | A61M 15/00 128/203.12 |
| 5,218,970 A | 6/1993 | Turnbull et al. | A61B 5/00 128/748 |
| 5,284,160 A | 2/1994 | Dryden | A61M 15/00 128/203.12 |
| 5,295,489 A | 3/1994 | Bell et al. | A61B 5/02 128/715 |
| 5,357,948 A | 10/1994 | Eilentropp | A61M 15/00 128/204.17 |
| 5,377,670 A | 1/1995 | Smith | A61M 16/00 128/204.17 |
| 5,387,117 A | 2/1995 | Moyher, Jr. et al. | H01R 4/60 439/191 |
| 5,392,770 A | 2/1995 | Clawson et al. | A61M 16/00 128/203.77 |
| 5,404,873 A | 4/1995 | Leagre et al. | A61M 16/00 128/204.18 |
| 5,416,270 A | 5/1995 | Kanao | F16L 11/11 174/47 |
| 5,454,061 A | 9/1995 | Carlson | H04B 3/40 392/478 |
| 5,485,870 A | 1/1996 | Kraik | F16L 11/10 138/122 |
| 5,526,849 A | 6/1996 | Gray | F16L 11/08 138/133 |
| 5,537,996 A | 7/1996 | McPhee | A61M 16/16 128/204.17 |
| 5,555,915 A | 9/1996 | Kanao | F16L 11/11 138/133 |
| 5,600,752 A | 2/1997 | Lopatinsky | A61M 16/00 392/488 |
| 5,601,119 A | 2/1997 | Kanao | F16L 11/118 138/133 |
| 5,636,806 A | 5/1997 | Inagaki et al. | A61M 25/00 604/282 |
| 5,637,168 A | 6/1997 | Carlson | B29C 47/02 156/143 |
| 5,640,951 A | 6/1997 | Huddart et al. | A61M 16/00 128/204.77 |
| 5,701,887 A | 12/1997 | Rustad et al. | A61M 16/00 128/204.17 |
| 5,715,815 A | 2/1998 | Lorenzen et al. | A62B 7/10 128/207.14 |
| 5,791,377 A | 8/1998 | LaRochelle | E03B 7/10 138/33 |
| 5,819,518 A | 10/1998 | Kanao | D02G 3/36 57/3 |
| 5,848,223 A | 12/1998 | Carlson | F24H 1/10 392/478 |
| 5,859,953 A | 1/1999 | Nickless | F16L 53/00 392/489 |
| 5,894,839 A | 4/1999 | Rosenkoetter et al. | A61M 16/00 128/200.24 |
| 5,974,227 A | 10/1999 | Schave | F24H 1/10 392/478 |
| 5,983,896 A | 11/1999 | Fukunaga et al. | A61M 16/00 128/207.14 |
| 5,988,164 A | 11/1999 | Paluch | A61M 16/00 128/203.26 |

(56) References Cited

U.S. PATENT DOCUMENTS

| | | | |
|---|---|---|---|
| 6,000,435 A | 12/1999 | Patel et al. | F16L 9/16 138/122 |
| 6,024,132 A | 2/2000 | Fujimoto | F16L 11/11 138/122 |
| 6,024,134 A | 2/2000 | Akedo et al. | F16L 11/04 138/129 |
| 6,029,660 A | 2/2000 | Calluaud et al. | A61M 15/00 128/203.12 |
| 6,050,260 A | 4/2000 | Daniell et al. | A61M 16/00 128/204.22 |
| 6,078,730 A | 6/2000 | Huddart et al. | F24H 1/10 392/480 |
| 6,103,971 A | 8/2000 | Sato et al. | F16L 11/04 174/47 |
| 6,105,576 A | 8/2000 | Clawson et al. | A62B 7/10 128/205.13 |
| 6,125,847 A | 10/2000 | Lin | A61M 16/00 128/204.17 |
| 6,129,082 A | 10/2000 | Leagre | A62B 7/10 128/205.29 |
| 6,148,818 A | 11/2000 | Pagan | A61M 16/00 128/207.15 |
| 6,152,186 A | 11/2000 | Arney et al. | F16L 11/08 138/129 |
| 6,167,883 B1 | 1/2001 | Beran et al. | A61M 16/00 128/203.17 |
| 6,186,183 B1 | 2/2001 | Lepoutre | F16L 11/12 138/125 |
| 6,190,480 B1 | 2/2001 | Carlson | B65H 81/00 156/143 |
| 6,219,490 B1 | 4/2001 | Gibertoni et al. | H05B 3/40 392/472 |
| 6,237,642 B1 | 5/2001 | Lepoutre | F16L 11/04 138/129 |
| 6,240,921 B1 | 6/2001 | Brydon et al. | A62B 7/00 128/205.23 |
| 6,272,933 B1 | 8/2001 | Gradon et al. | G01F 1/00 73/861 |
| 6,305,428 B1 | 10/2001 | Nakamura et al. | F16L 11/10 138/126 |
| 6,347,646 B2 | 2/2002 | Fukui | F16L 11/00 138/129 |
| 6,349,722 B1 | 2/2002 | Gradon et al. | A61M 15/00 128/203.17 |
| 6,363,930 B1 | 4/2002 | Clawson et al. | A62B 18/08 128/201.13 |
| 6,367,510 B1 | 4/2002 | Carlson | F16L 11/08 138/121 |
| 6,378,520 B1 | 4/2002 | Davenport | A61M 16/00 128/204.26 |
| 6,394,084 B1 | 5/2002 | Nitta | A62B 18/08 128/201.13 |
| 6,394,143 B1 | 5/2002 | Diels et al. | F16L 11/11 138/121 |
| 6,397,841 B1 | 6/2002 | Kenyon et al. | A62B 18/00 |
| 6,536,428 B1 | 3/2003 | Smith et al. | A61M 16/00 128/203.17 |
| 6,554,260 B1 | 4/2003 | Lipscombe et al. | B01F 3/04 261/142 |
| 6,584,972 B2 | 7/2003 | McPhee | A61M 15/00 128/203.17 |
| 6,659,136 B2 | 12/2003 | Fukui et al. | F16L 11/00 138/125 |
| 6,662,802 B2 | 12/2003 | Smith et al. | A61M 15/00 128/203.16 |
| 6,694,974 B1 | 2/2004 | GeorgeGradon et al. | A61M 15/00 128/203.17 |
| 6,718,973 B2 | 4/2004 | Koch | A61M 15/00 128/203.16 |
| 6,769,431 B2 | 8/2004 | Smith et al. | B01D 53/22 128/203.16 |
| 6,827,109 B2 | 12/2004 | McCaughtry | F16L 11/08 138/134 |
| 6,874,500 B2 | 4/2005 | Fukunaga et al. | A61M 16/00 128/204.18 |
| 6,918,389 B2 | 7/2005 | Seakins et al. | H05B 3/00 128/203.27 |
| 6,932,119 B2 | 8/2005 | Carlson | F16L 11/12 138/121 |
| 6,935,337 B2 | 8/2005 | Virr et al. | A61M 15/00 128/203.16 |
| 6,939,424 B1 | 9/2005 | Takala et al. | B65B 81/00 156/191 |
| 6,948,527 B2 | 9/2005 | Ragner et al. | F16L 11/00 138/119 |
| 6,953,354 B2 | 10/2005 | Edirisuriya et al. | H01R 4/60 439/191 |
| 7,086,422 B2 | 8/2006 | Huber et al. | F16L 9/14 138/149 |
| 7,096,864 B1 | 8/2006 | Mayer et al. | A62B 9/04 128/202.27 |
| 7,120,354 B2 | 10/2006 | Mackie et al. | F24H 1/10 392/480 |
| 7,137,388 B2 | 11/2006 | Virr et al. | A61M 11/00 128/203.17 |
| 7,144,473 B2 | 12/2006 | Baecke | B01D 1/00 159/47.1 |
| 7,156,127 B2 | 1/2007 | Moulton et al. | F16L 11/112 138/122 |
| 7,178,521 B2 | 2/2007 | Burrow et al. | A62B 9/04 128/202.27 |
| 7,275,541 B2 | 10/2007 | Fukunaga et al. | A61M 16/00 128/204.18 |
| 7,291,240 B2 | 11/2007 | Smith et al. | B65H 81/00 156/195 |
| 7,383,745 B2 | 6/2008 | Eiteneer et al. | G01N 1/00 73/863.12 |
| 7,418,965 B2 | 9/2008 | Fukunaga et al. | A61M 16/00 128/204.18 |
| 7,418,980 B2 | 9/2008 | Lee | F16L 11/08 138/121 |
| 7,431,054 B2 | 10/2008 | Kramer, Jr. et al. | F16L 9/14 138/133 |
| 7,468,116 B2 | 12/2008 | Smith et al. | B32B 37/00 156/344 |
| 7,469,719 B2 | 12/2008 | Gray | F16L 53/00 138/33 |
| 7,478,635 B2 | 1/2009 | Wixey et al. | A61M 11/00 128/203.17 |
| 7,520,302 B2 | 4/2009 | Smith | F16L 11/118 138/118 |
| 7,575,005 B2 | 8/2009 | Mumford et al. | A62B 9/00 128/205.23 |
| 7,588,029 B2 | 9/2009 | Smith et al. | A61M 15/00 128/203.17 |
| 7,597,119 B2 | 10/2009 | Boettner | F16L 11/12 138/119 |
| 7,721,766 B2 | 5/2010 | Sawada | F16L 53/00 138/22 |
| 7,735,523 B2 | 6/2010 | Smith et al. | F16L 11/00 138/118 |
| 7,856,981 B2 | 12/2010 | NcAnley et al. | A61M 15/00 128/207.13 |
| 7,958,891 B2 | 6/2011 | Smith et al. | A62B 18/08 128/203.16 |
| 7,962,018 B2 | 6/2011 | Hunt et al. | F24F 6/00 392/394 |
| 7,965,930 B2 | 6/2011 | Carlson et al. | F24H 1/10 392/478 |
| 7,991,273 B2 | 8/2011 | Sonderegger et al. | F24H 1/10 392/478 |
| 8,006,691 B2 | 8/2011 | Kenyon et al. | A62B 9/00 128/200.24 |
| 8,015,971 B2 | 9/2011 | Kwok | A61M 16/00 128/204.17 |
| 8,020,557 B2 | 9/2011 | Bordewick et al. | A61M 11/00 128/206.18 |

(56) References Cited

U.S. PATENT DOCUMENTS

| | | | |
|---|---|---|---|
| 8,028,721 B2 | 10/2011 | Koskey, Jr. | F16L 53/00 138/33 |
| 8,063,343 B2 | 11/2011 | McGhin et al. | H05B 1/02 219/497 |
| 8,078,040 B2 | 12/2011 | Forrester | F24H 1/10 392/481 |
| 8,186,345 B2 | 4/2012 | Payton et al. | A61M 11/00 128/204.17 |
| 8,210,173 B2 | 7/2012 | Vandine | A61B 5/08 128/204.21 |
| 8,238,733 B2 | 8/2012 | Sawada et al. | F24H 1/10 392/488 |
| 8,291,939 B2 | 10/2012 | Ferrone | F16L 53/00 138/33 |
| 8,333,195 B2 | 12/2012 | Cortez, Jr. et al. | F23D 11/00 |
| 8,360,059 B2 | 1/2013 | Koulechov et al. | A61M 16/00 |
| 8,453,641 B2 | 6/2013 | Payton et al. | A61M 11/00 128/204.17 |
| 8,453,681 B2 | 6/2013 | Forrester et al. | F16L 11/118 138/122 |
| 8,529,719 B2 | 9/2013 | Pingleton et al. | B32B 37/00 156/173 |
| 8,544,504 B2 | 10/2013 | Castro | F16L 11/00 138/121 |
| 8,550,075 B2 | 10/2013 | Virr | A61M 16/16 128/203.27 |
| 8,563,863 B2 | 10/2013 | Carlson | H01B 7/18 174/108 |
| 8,563,864 B2 | 10/2013 | Carlson | H01B 7/18 174/108 |
| 8,631,789 B2 | 1/2014 | Virr et al. | A61M 15/00 128/204.18 |
| 8,691,035 B2 | 4/2014 | Pingleton et al. | A61M 25/01 156/172 |
| 8,709,187 B2 | 4/2014 | Smith et al. | B31C 1/00 156/184 |
| 8,715,441 B2 | 5/2014 | Brustad et al. | B29C 65/02 156/143 |
| 8,726,901 B2 | 5/2014 | Jassell et al. | A61M 16/08 128/204.17 |
| 8,739,780 B2 | 6/2014 | Tang et al. | A61M 11/00 128/203.14 |
| 8,776,836 B2 | 7/2014 | Ragner et al. | F16L 11/00 138/119 |
| 8,833,367 B2 | 9/2014 | Kwok | A61M 16/10 128/204.22 |
| 8,863,782 B2 | 10/2014 | Rerrone | F16L 53/00 138/33 |
| 8,890,039 B2 | 11/2014 | Etscheid et al. | F16L 53/00 219/492 |
| 8,893,715 B2 | 11/2014 | Payton et al. | F23D 14/00 128/204.18 |
| 8,905,082 B2 | 12/2014 | Gray | F16L 11/00 138/109 |
| 8,965,187 B2 | 2/2015 | Borgmeier et al. | F16L 11/12 392/480 |
| 8,985,105 B2 | 3/2015 | Burton et al. | F16K 31/02 128/203.12 |
| 9,022,036 B2 | 5/2015 | Graham et al. | A61M 16/00 128/207.14 |
| 9,077,134 B2 | 7/2015 | Ferrone | H01R 43/00 138/33 |
| 9,186,477 B2 | 11/2015 | Hunt et al. | F24F 6/00 128/203 |
| 9,206,934 B2 | 12/2015 | Reusche et al. | F16L 11/12 138/33 |
| 9,272,114 B2 | 3/2016 | Herron | A61M 16/00 138/33 |
| 9,295,801 B2 | 3/2016 | Graham et al. | A61M 16/08 128/203.26 |
| 9,308,698 B2 | 4/2016 | Forrester et al. | B29D 23/18 156/143 |
| 9,322,501 B2 | 4/2016 | Carlson | F16L 53/004 392/478 |
| 9,358,316 B2 | 6/2016 | Leyva | A61L 2/20 422/28 |
| 9,365,004 B2 | 6/2016 | Forrester | F16L 11/115 156/143 |
| D761,422 S | 7/2016 | Row et al. | D24/129 |
| D762,843 S | 8/2016 | Formica et al. | A61M 16/0616 D24/110 |
| 9,464,747 B2 | 10/2016 | Eckardt et al. | F16L 53/00 138/32 |
| 9,505,164 B2 | 11/2016 | Garrett et al. | B29C 53/582 156/244.11 |
| 9,506,595 B2 | 11/2016 | Eckardt et al. | F16L 53/00 |
| 9,533,117 B2 | 1/2017 | Gray | A61M 16/0883 138/33 |
| 9,556,978 B2 | 1/2017 | Garrett et al. | F16L 11/24 138/122 |
| 9,566,408 B2 | 2/2017 | Henry | A61M 16/00 128/205.25 |
| 9,624,806 B2 | 4/2017 | Mann | F24H 1/10 392/485 |
| 9,625,066 B2 | 4/2017 | Carlson et al. | F16L 11/24 138/122 |
| 9,638,359 B2 | 5/2017 | Rothfuss | F16L 11/16 138/134 |
| 9,642,979 B2 | 5/2017 | Korneff et al. | A61M 16/1095 |
| 9,656,038 B2 | 5/2017 | Rummery et al. | A61M 16/0875 138/121 |
| 9,664,086 B2 | 5/2017 | Birman et al. | F01N 3/2896 392/485 |
| 9,671,053 B2 | 6/2017 | Eckardt et al. | F16L 53/008 392/485 |
| 9,702,492 B2 | 7/2017 | Borgmeier et al. | F16L 39/00 285/41 |
| 9,707,370 B2 | 7/2017 | Smith et al. | A61M 11/00 128/203.26 |
| 9,717,874 B2 | 8/2017 | Smith et al. | A61M 16/0875 428/139 |
| RE46,543 E | 9/2017 | TrevorWilson et al. | A61M 16/00 |
| D798,428 S | 9/2017 | Cork et al. | B01D 46/02 D23/360 |
| 9,750,916 B2 | 9/2017 | Magee | A61M 16/10 261/142 |
| 9,765,909 B2 | 9/2017 | Ashcroft | F16L 11/12 138/118 |
| RE46,571 E | 10/2017 | Virr et al. | A61M 16/16 |
| 9,784,387 B2 | 10/2017 | Kaye et al. | F16L 11/1185 138/109.96 |
| 9,802,015 B2 | 10/2017 | Virr et al. | A61M 16/00 128/204.23 |
| 9,821,135 B2 | 11/2017 | Tang et al. | A61M 16/16 128/202.22 |
| 9,989,174 B2 * | 6/2018 | Garrett | A47L 9/248 |
| 2002/0148522 A1 | 10/2002 | Hupertz et al. | F16L 11/16 138/135 |
| 2003/0098084 A1 | 5/2003 | Ragner et al. | F16L 11/00 138/129 |
| 2004/0007278 A1 | 1/2004 | Williams | A47L 9/24 138/131 |
| 2004/0079371 A1 | 4/2004 | Gray | A61M 16/00 |
| 2004/0081784 A1 * | 4/2004 | Smith | A61M 11/08 428/36.9 |
| 2006/0011249 A1 | 1/2006 | Arima et al. | F16L 11/00 138/109 |
| 2006/0051547 A1 | 3/2006 | Lim | B29C 53/582 428/204.17 |
| 2006/0070679 A1 | 4/2006 | Ragner | F16L 11/00 138/119 |
| 2006/0165829 A1 | 7/2006 | Smith et al. | B29C 47/00 425/113 |
| 2007/0252292 A1 | 11/2007 | Sondergger et al. | H01R 4/60 439/191 |

(56) References Cited

U.S. PATENT DOCUMENTS

| | | | |
|---|---|---|---|
| 2007/0283958 A1 | 12/2007 | Haghavi | A61M 16/00 128/204.18 |
| 2008/0000474 A1 | 1/2008 | Jochle et al. | A61M 16/00 128/204.18 |
| 2008/0035229 A1 | 2/2008 | Kramer et al. | F16L 11/00 138/132 |
| 2009/0050227 A1 | 2/2009 | Smith | F16L 11/00 138/122 |
| 2009/0078259 A1 | 3/2009 | Kooij et al. | A62B 18/02 128/205.25 |
| 2009/0078440 A1 | 3/2009 | Carlson et al. | F16L 11/12 174/47 |
| 2009/0277525 A1 | 11/2009 | Jourdan et al. | A47L 9/248 138/122 |
| 2010/0108170 A1 | 5/2010 | Chudkosky et al. | F16L 11/11 138/122 |
| 2010/0139661 A1 | 6/2010 | Landis | A62B 18/02 128/205.25 |
| 2010/0215351 A1 | 8/2010 | Forrester et al. | F24H 1/10 392/481 |
| 2010/0224276 A1 | 9/2010 | Forrester | A47L 9/248 138/122 |
| 2011/0005661 A1 | 1/2011 | Brustad et al. | B29D 23/20 156/143 |
| 2011/0006513 A1 | 1/2011 | Lechner et al. | F16L 41/00 285/122.1 |
| 2011/0108031 A1 | 5/2011 | Korneff et al. | A61M 16/16 128/203.27 |
| 2012/0247619 A1 | 10/2012 | Formica et al. | 128/204.18 |
| 2012/0291783 A1 | 11/2012 | Peiris et al. | A61M 16/00 128/204.21 |
| 2013/0068334 A1 | 3/2013 | Diels | F16L 11/24 138/129 |
| 2013/0098260 A1 | 4/2013 | Hurmez et al. | A61M 16/16 128/203.12 |
| 2013/0152931 A1 | 6/2013 | Sims et al. | A61M 16/08 128/204.17 |
| 2013/0233318 A1 | 9/2013 | Graham et al. | A61M 16/08 128/305.27 |
| 2013/0306075 A1 | 11/2013 | Payton et al. | A61M 16/00 128/205.23 |
| 2014/0053939 A1 | 2/2014 | Kaye et al. | F16L 11/1185 138/109 |
| 2014/0076605 A1 | 3/2014 | Diels et al. | F16L 11/16 174/98 |
| 2014/0158125 A1 | 6/2014 | O'Donnell et al. | A61L 2/24 128/203.14 |
| 2014/0202462 A1 | 7/2014 | Stoks et al. | A61M 25/00 128/204.18 |
| 2014/0236083 A1 | 8/2014 | Sims | A61M 16/10 604/114 |
| 2014/0238397 A1 | 8/2014 | Buechi et al. | A61M 16/1095 128/203.27 |
| 2014/0311487 A1 | 10/2014 | Buechi et al. | A61M 16/08 128/203.14 |
| 2014/0326395 A1 | 11/2014 | Forrester | B29D 23/18 156/195 |
| 2014/0332108 A1 | 11/2014 | Forrester et al. | F16L 11/112 138/122 |
| 2014/0366979 A1 | 12/2014 | Mollen | F16L 11/08 138/138 |
| 2014/0373843 A1 | 12/2014 | Gray | A61M 16/08 128/204.17 |
| 2015/0020801 A1 | 1/2015 | Frame et al. | A61M 16/00 128/202.22 |
| 2015/0059908 A1 | 3/2015 | Mollen | F16L 11/08 138/132 |
| 2015/0108670 A1 | 4/2015 | Magee | A61M 16/1045 |
| 2015/0128944 A1 | 5/2015 | Buechi | A61M 16/10 |
| 2015/0165157 A1 | 6/2015 | Payton et al. | A61M 16/16 |
| 2015/0202402 A1 | 7/2015 | Kat | A61M 16/16 |
| 2015/0217079 A1 | 8/2015 | Meauley et al. | A61M 16/10 |
| 2015/0283350 A1 | 10/2015 | Miller et al. | A61M 16/08 |
| 2016/0193437 A1 | 7/2016 | Bao et al. | A61M 16/00 |
| 2017/0000968 A1 | 1/2017 | Harrington | A61M 16/16 |
| 2017/0182280 A1 | 6/2017 | Leonard | A61M 16/145 |
| 2017/0197055 A1 | 7/2017 | Moody et al. | A61M 16/08 |

FOREIGN PATENT DOCUMENTS

| | | | |
|---|---|---|---|
| DE | 4039215 A1 | 12/1990 | B29D 23/22 |
| DE | 29507806 U2 | 5/1995 | F16L 11/127 |
| DE | 69527528 T2 | 5/1995 | F24H 1/10 |
| DE | 19737676 C1 | 8/1997 | F16L 11/12 |
| DE | 19752008 A1 | 11/1997 | A47L 9/24 |
| DE | 19904864 A1 | 2/1999 | E21B 7/26 |
| DE | 19949283 A1 | 10/1999 | A61M 16/08 |
| DE | 202005013 786 | 12/2005 | F16L 11/24 |
| DE | 102006023459 A1 | 10/2006 | F16L 37/14 |
| DE | 102008022663.7 | 5/2008 | F16L 11/12 |
| DE | 102009009790 B3 | 2/2009 | F16L 11/11 |
| DE | 102013109362 A1 | 8/2013 | F16L 11/04 |
| DE | 102013106164 A1 | 12/2014 | F16L 11/127 |
| EP | 0097901 | 6/1983 | F16L 11/11 |
| EP | 0201985 | 2/1986 | A61M 16/08 |
| EP | 0742399 | 5/1996 | F16L 11/127 |
| EP | 0917851 | 11/1997 | A47L 9/24 |
| EP | 1181945 A1 | 9/2002 | A61M 16/10 |
| WO | WO 2004/011072 | 5/1995 | A61M 16/00 |
| WO | WO 95/33163 | 12/1995 | F24H 1/10 |
| WO | WO 98/04311 | 2/1998 | |
| WO | WO 02/38426 | 5/2002 | |
| WO | WO 2004/024429 | 3/2004 | B29C 53/02 |
| WO | WO 2006/094576 | 1/2006 | A61M 16/10 |
| WO | WO 2007/101298 | 9/2007 | |
| WO | WO 2009/103869 | 8/2009 | |
| WO | WO 2011/151008 | 12/2011 | |
| WO | WO 2014/044499 | 3/2014 | |

* cited by examiner

STRETCH HOSE AND HOSE PRODUCTION METHOD

CROSS-REFERENCE TO RELATED PATENTS AND APPLICATIONS

This application is a division of Ser. No. 15/530,530 filed Jan. 25, 2017 entitled STRETCH HOSE AND HOSE PRODUCTION METHOD which was filed as a division of application Ser. No. 14/544,767 filed Feb. 16, 2015 also entitled STRETCH HOSE AND HOSE PRODUCTION METHOD which issued Jan. 31, 2017 as U.S. Pat. No. 9,556,978, which application not only claimed the benefit of the filing date of provisional Ser. No. 61/966,171 filed Feb. 18, 2014 entitled STRETCH HOSE AND METHOD OF HOSE PRODUCTION but also was a continuation-in-part of each of two then-pending applications, namely:

1) Ser. No. 13/986,465 filed May 6, 2013 entitled METHOD OF HOSE MANUFACTURE which issued Apr. 12, 2016 as U.S. Pat. No. 9,308,698 which application was filed as a continuation of application Ser. No. 12/779,263 filed Apr. 21, 2010 entitled FLEXIBLE, STRETCHABLE, CRUSH RESISTANT HOSE WELL SUITED FOR MEDICAL APPLICATIONS which issued Jun. 4, 2013 as U.S. Pat. No. 8,453,681 that not only claimed the benefit of the filing date of provisional Ser. No. 61/335,023 filed Dec. 30, 2009 entitled FLEXIBLE HOSE FOR MEDICAL APPLICATIONS but also was filed as a continuation-in-part of application Ser. No. 12/354,291 filed Jan. 15, 2009 entitled STRETCH HOSE (abandoned); and, 2) Ser. No. 13/507,172 filed Jun. 11, 2012 entitled TAPERED HELICALLY REINFORCED HOSE AND ITS MANUFACTURE which not only issued Nov. 29, 2016 as U.S. Pat. No. 9,505,164 but also claimed the benefit of the filing date of provisional application Ser. No. 61/627,425 filed Oct. 12, 2011 entitled TAPERED FLEXIBLE HOSE AND METHOD OF MANUFACTURE.

The disclosures of all of the patents and applications listed above are incorporated herein by reference.

FIELD OF THE INVENTION

The present invention relates to a flexible, extensible and retractable, helically reinforced, corrugated hose continuously formed from freshly extruded thermoplastic material fed to and helically wound in a coordinated manner around a rotating mandrel. The freshly extruded material remains tacky during hose formation so that each new wrap of the freshly extruded material bonds to a previous wrap. When stretched, the resulting hose has a thin web-defined wall that extends between each adjacent pair of the reinforcing coils—a wall that has two spaced portions, one that bends or folds radially inwardly, and other of which bends or folds radially outwardly, thereby permitting use of a wide extruded web that gives the resulting hose a desirably high stretch ratio of fully extended to fully axially compressed lengths.

Discrete lengths of the resulting hose are preferably treated during a secondary production process while being axially compressed to minimal axial length—to minimize stress and to reset the memory of the thermoplastic material, yielding a superbly flexible and splendidly drapable product.

BACKGROUND

Disclosed in U.S. Pat. No. 3,966,525 issued Jun. 29, 1976 to William L. Steward (the disclosure of which is incorporated herein by reference), is a now commonly employed technique whereby freshly extruded thermoplastic materials are wound onto a rotating mandrel to continuously produce spirally reinforced stretch hose. As the Steward patent explains, a tape-like web of thermoplastic material of substantially uniform width and thickness, and a bead of thermoplastic material of substantially uniform cross-section are extruded concurrently and continuously in a direction toward, and are helically wrapped onto, or wound about, a turning mandrel.

The tacky, freshly extruded thermoplastic materials overlap sufficiently as they are fed onto the rotating mandrel to cause seam-free bonding that produces helically reinforced extensible-retractable stretch hose in a continuous manner. The newly formed hose has a continuous set of helically wound reinforcing coils that are defined by the bead material, with the web material also being helically wound into position bridging between and connecting each adjacent pair of the reinforcing coils. As the mandrel turns, the newly formed stretch hose is caused to rotate as the hose precesses along the mandrel's length. The hose eventually discharges from a distal end region of the mandrel.

Disclosed in the above-referenced U.S. Pat. No. 8,453,681 issued Jun. 4, 2013 to Martin Forrester et al (referred to hereinafter as the Annealing System Patent, the disclosure of which is incorporated herein by reference) is the use of an annealing process that treats discrete lengths of newly produced stretch hose while the discrete lengths are fully axially compressed. Such annealing resets the memory of the thermoplastic material forming the stretch hose, causing discrete lengths of the hose that are stretched or extended, to retract to minimal length when forces causing the hose lengths to extend are released—and causes hose lengths are bent while being stretched, to straighten as they retract toward their minimal axial lengths.

Application Ser. No. 13/507,172 discloses that "stretch hose" formed by continuously wrapping extruded thermoplastic materials about mandrels (that include a plurality of elongate rods which rotate in unison) can be caused to change in cross-sectional dimension (i.e., to increase or to decrease hose diameter) as hose is continuously formed.

Application Ser. No. 13/987,837 discloses that "stretch hose" can be formed continuously by wrapping extruded materials about rotating mandrels, with adjacent pairs of reinforcing coils having their inner diameter regions connected one to the next by thin webs that are sandwiched between the adjacent reinforcing coils when the hose is axially compressed.

None of the several above-referenced documents disclose the production of hose having a web that extends in an inclined spiral from an outer diameter of each reinforcing coil to the inner diameter of an adjacent reinforcing coil, thereby giving the hose something of a thread-like exterior appearance. None of the several documents referenced above discloses a stretch hose having a thin web that advantageously assumes the kind of "double fold" that occurs when hose embodying the preferred practice of the present invention is axially compressed.

SUMMARY

One aspect of the present invention relates to the continuous production of crush resistant, extensible and retractable, helically reinforced, axially extending hose formed as freshly extruded thermoplastic materials are fed to and wound in a uniquely coordinated manner about a rotating mandrel, with the freshly extruded thermoplastic materials bonding to still-tacky thermoplastic materials extruded only a moment previously.

One aspect of the present invention resides in the production of stretch hose having each adjacent pair of reinforcing coils joined by a thin, web-defined wall that forms a slanted spiral which gives the newly-formed hose something of a thread-like exterior appearance. When the hose is axially compressed, the thin web-defined walls that connect each adjacent pair of the reinforcing coils have central portions that are sandwiched between the reinforcing coils, and two other portions, one of which bends or folds radially outwardly, and other of which bends or folds radially inwardly—and yet, the internal diameter of the hose, when compressed, is not unduly diminished, and the external diameter, when compressed, is not unduly increased.

Some embodiments call for the newly extruded web to be unusually wide so that, when the resulting hose is axially extended, the thin, web-defined walls unfold and straighten, causing the fully extended hose to exhibit an unusual length—which means the hose has an unusually large stretch ratio of its fully axially extended length to its fully axially compressed length. Forming stretch hose using an unusually wide extruded web also enables the resulting hose to bend through tight turns, and contributes to the ability of the hose to extend through confined spaces.

In some embodiments, the bead and the web of thermoplastics material are separately extruded, and bonding of the bead and the web begins before the bead and the web reach the rotating mandrel. A remainder of the bonding needed to continuously form the stretch hose occurs as the tacky web and tacky bead engage a still-tacky previously wrapped bead that forms a reinforcing coil on the rotating mandrel. Separate extrusion of the bead and web permits different thermoplastic materials to be used to form the bead and web.

In some embodiments, the extruded bead that forms the helically wound reinforcing coils is made from a harder, somewhat stiffer thermoplastic than the thermoplastic selected to form the extruded web which bridges between and connects adjacent pairs of the reinforcing coils. The harder, stiffer plastic material that forms the reinforcing coils adds strength to, and improves the pressure and vacuum ratings of the resulting hose, as well as the crush resistance of the hose.

In some embodiments, the web that extends between and connects each adjacent pair of helically wound reinforcing coils has one of its two opposite edge regions bonded to a radially outermost-located surface defined by one of the two adjacent reinforcing coils, and has the other of its two opposite edge regions bonded to a radially innermost-located surface defined by the other of its two adjacent reinforcing coils. This arrangement causes the thin web-defined walls that connect the adjacent pairs of reinforcing coils to behave in a unique and advantageous manner when the hose retracts or is axially compressed—in that the thin connecting walls execute a "double fold" by bending or folding radially inwardly at one location, and by bending or folding radially outwardly at another location, with an in-between or connecting central region of each connecting wall extending in an inclined manner between the associated reinforcing coils (until being compressively sandwiched between the associated reinforcing coils when the hose is axially compressed).

Still other aspects of the invention reside in providing discrete lengths of the continuously formed hose with enhanced physical and behavioral characteristics that are induced by a secondary treatment process performed while the discrete hose lengths are fully axially compressed. This secondary treatment process relieves stress, resets the memory of the hose to a fully axially compressed state, and greatly improves the flexibility of the hose. Annealing is one such treatment. Radiation exposure and other stress-reducing, memory resetting processes may also be used that reduce hose stiffness to provide a superbly flexible and desirably drapable product.

BRIEF DESCRIPTION OF THE DRAWINGS

Features of, and a fuller understanding of the invention will be better obtained by referring to the description and claims that follow, taken in conjunction with the accompanying drawings, wherein:

DESCRIPTION

Figure 1:
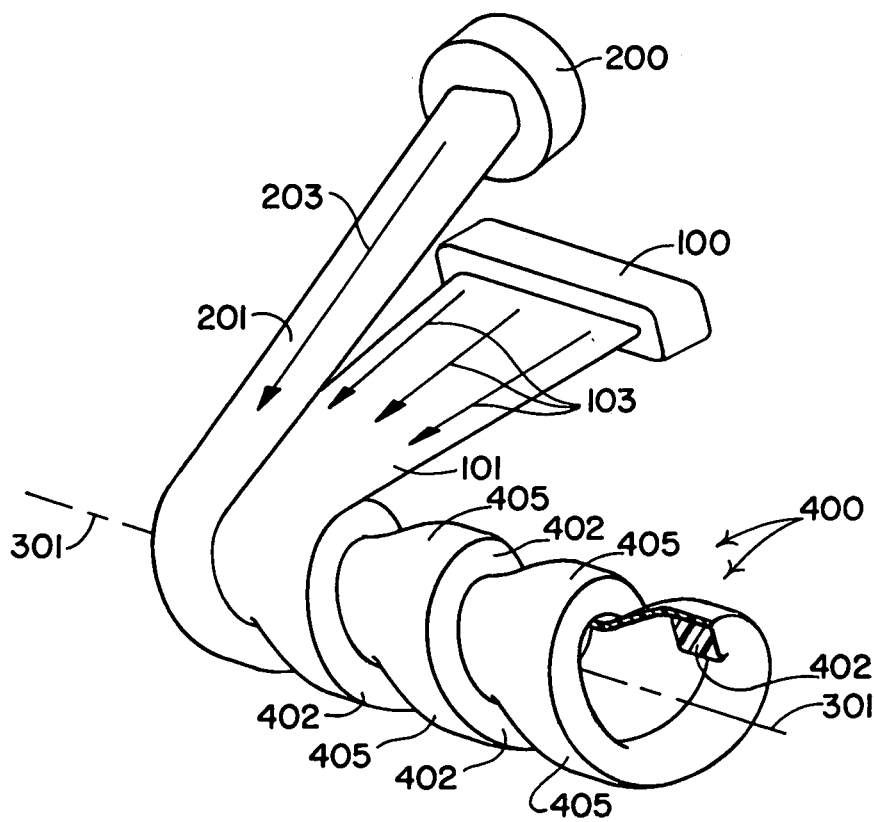
FIG. 1 is a schematic illustration showing a preferred process by which a separately extruded bead and thin web of thermoplastics material are continuously fed, to a rotating mandrel (that is indicated simply by a centerline of the mandrel, since the rotating mandrel may take many conventional forms typically comprising a single elongate, cylindrical, rotating rod, or a plurality of elongate, cylindrical rods that are rotated in unison about the depicted centerline), with the freshly extruded thermoplastics material being helically wound in a coordinated manner about the rotating mandrel to continuously produce reinforced hose that precesses forwardly (in a rightward direction along the depicted centerline) along the rotating mandrel away from the location where winding of the thermoplastic material takes place—with the single arrow extending along the centerline of the mandrel indicating a direction of flow of a bead of extruded thermoplastic material that forms helical reinforcing coils, and with the three side-by-side arrows indicating a direction of flow of a thin, substantially flat web of substantially uniform thickness that forms a sidewall of the hose resulting hose.

A preferred production method of the present invention for forming stretch hose from thermoplastic material is schematically depicted in FIGS. 1-4. Referring to FIGS. 1-4, separate extrusion dies are indicated by the numerals 100 and 200. Thermoplastic material in the form of a relatively thin, tape-like web 101 is continuously extruded from the extrusion die 100. Thermoplastic material in the form of a relatively thick bead of preferably generally rectangular cross-section 201 is extruded continuously from the extrusion die 201.

The extruded web 101 and the extruded bead 201 preferably each have substantially uniform cross-sections along their lengths. Although the web 101 almost always has a simple, thin, tape-like cross-section, the bead 201 may take a variety of selected cross-sectional configurations that include, for example, a substantially square cross-section, a substantially round cross-section, and a substantially elliptical cross-section. Other bead cross-sections can be selected to form hose that is engineered for use in specific applications. The depicted generally rectangular cross-section has the advantage of providing both radially outwardly facing, and radially inwardly facing surfaces that are relatively flat and sizable, to which opposite edge regions of the freshly extruded, thin, tape-like web 101 can quickly and securely bond while the web 101 and the bead 201 are still tacky.

In preferred practice, the thermoplastic material that is heated and extruded through the extrusion dies 100, 200 is preferably an opaque thermoplastic of uniform consistency. By providing separate extrusion dies 100, 200 for the web 101 and the bead 201, respectively, different thermoplastic materials can be used to provide the web 101 and the bead 201 that form the resulting hose 400. Alternately, substantially the same thermoplastic material can be extruded from each of the extrusion dies 100, 200 to provide the web 101 and the bead 201 that form the resulting hose 400.

Figure 2:
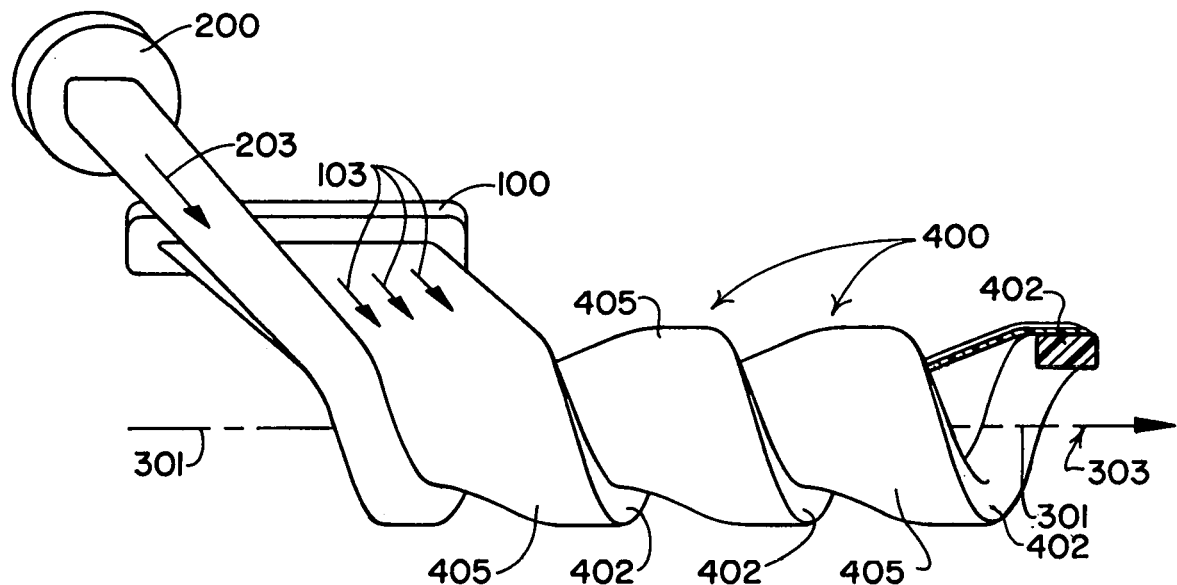
FIG. 2 is a front view of the hose production method shown schematically in FIG. 1, with this front view helping to show how the inclined helix formed by the extruded web extends from an outer diameter region of each reinforcing coil to an inner diameter region of a next-formed reinforcing coil, thereby giving the resulting hose something of a thread-like exterior appearance.
Figure 3:
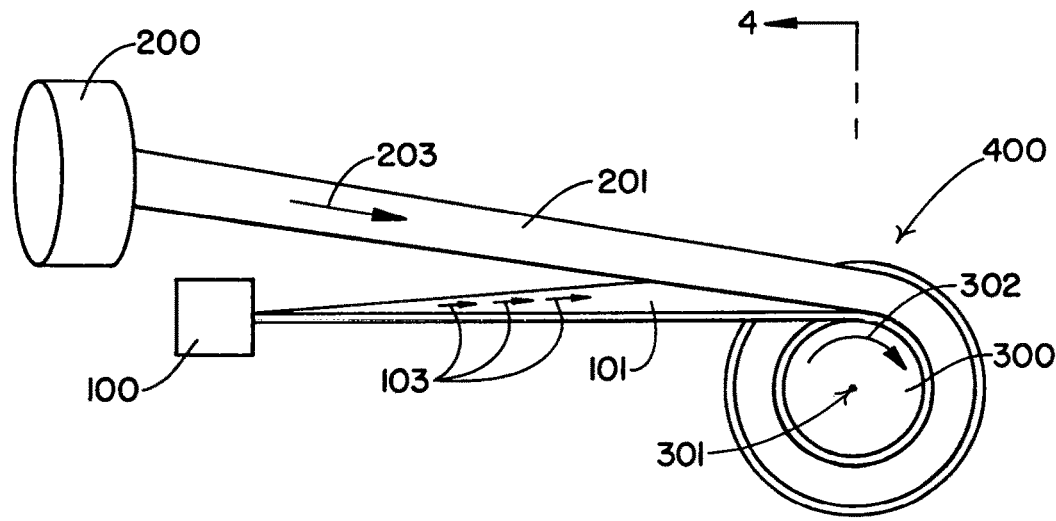
FIG. 3 is an end view of the hose production method depicted schematically in FIGS. 1 and 2 as seen from the upstream end of a depicted single-rod mandrel, with a single curved arrow indicating a direction of rotation of the mandrel about which the freshly extruded bead and web are helically wrapped.

Referring to FIGS. 1-3, the freshly extruded web 101 and freshly extruded bead 201 are fed toward a rotating mandrel 300 in a coordinated manner indicated by arrows 103, 203, respectively. The mandrel 300 turns about a centerline 301 in a direction of rotation indicated in FIG. 3 by a curved arrow 302. As the freshly extruded web 101 and the bead 201 come into contact with each other, their heated, tacky nature causes the web 101 and the bead 201 to begin bonding one to another almost immediately. As the web 101 and the bead 201 are wound onto the rotating mandrel 300, the rotation of the mandrel 300 helps to draw the web 101 and the bead 201 onto the mandrel 300.

Although the mandrel 300 is shown as taking the form of a single rotating rod or shaft of constant diameter, the mandrel 300 typically consists of a circular array of solid or flexible shafts that turn in unison about the axis 301. The rods that form the mandrel 300 are typically arranged at an angle that causes the the web 101, the bead 201 and the newly formed hose 400 to precess along the mandrel 300 toward a distal end of the mandrel 300—as is explained in the referenced Steward U.S. Pat. No. 3,966,525, and in the referenced application of Garrett, Hadley and Forrester. These types of hose forming mandrels are well known to those who are skilled in the art, and are not the subject of the current invention.

As the mandrel 300 turns, the web 101 and the bead 201 are helically wrapped in a coordinated manner around the mandrel 300 that causes a particularly desirable type of stretch hose 400 to be continuously formed. The newly formed hose 400 precesses forwardly along the rotating mandrel 300 in a direction indicated by an arrow 303 in FIGS. 3 and 4. As the hose 400 reaches a distal end of the mandrel 300, the newly produced hose 400 typically is cooled and conveyed to an automatic cutter (not shown) where the hose 400 is cut into discrete lengths for further processing, as will be explained.

Figure 4:
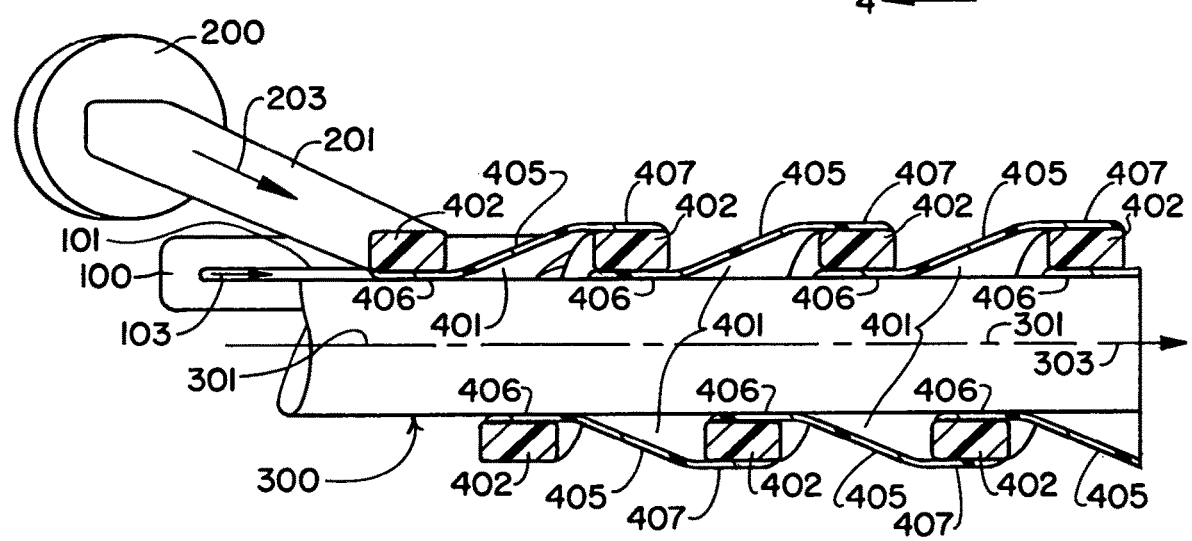
FIG. 4 is a cross-sectional view as seen from a plane indicated by a line 4-4 in FIG. 3, with the view more clearly showing how the web of the newly formed hose extends from an outer diameter region of a leading one of each adjacent pair of reinforcing coils to an inner diameter region of a next-formed or trailing one of each adjacent pair of reinforcing coils, with an arrow extending along the centerline of the mandrel indicating a forward direction of precession of the newly formed hose.
Figure 5:
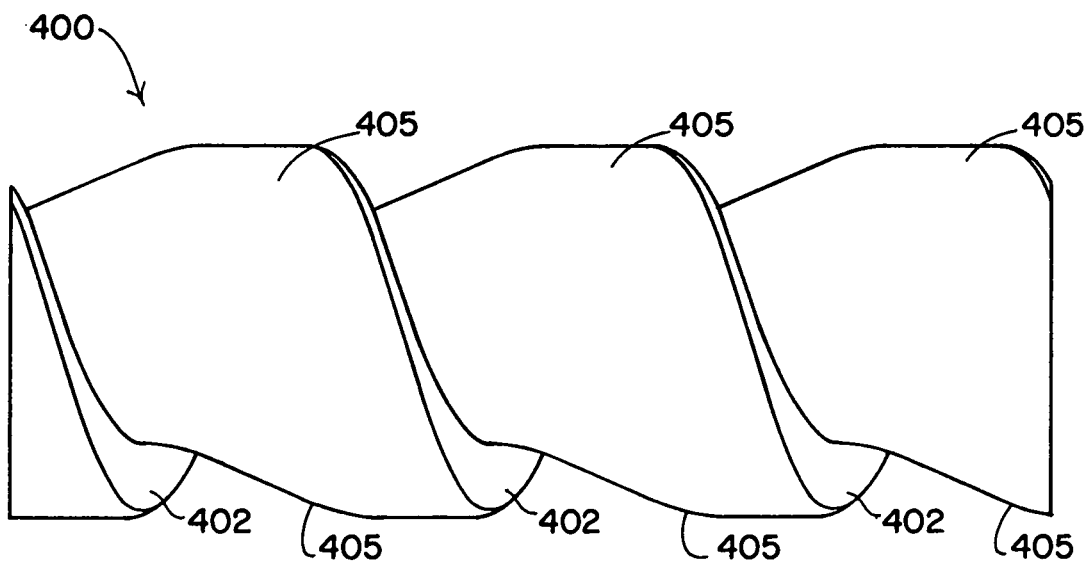
FIG. 5 is a front view showing a length of newly formed hose in a fully extended state, as the hose is continuously formed in accordance with the hose production process depicted in FIGS. 1-4.
Figure 6:
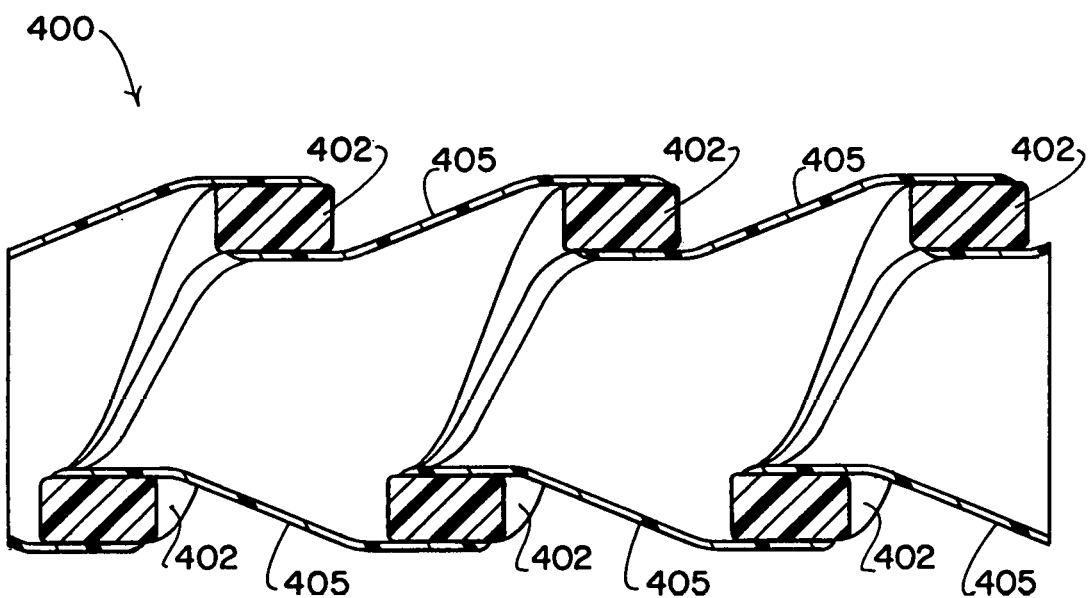
FIG. 6 is a sectional view of the length of fully extended hose shown in FIG. 5, but with a front half of the hose broken away, and with the rear half of the hose length shown in cross-section.

The cross-sectional configuration of the newly formed hose 400 can be seen in FIG. 4. The hose 400 is formed by relatively thin, flexible walls' 405, and relatively thick reinforcing coils 402. The relatively thin, flexible walls 405 are components of an inclined spiral of web material that is formed by the relatively thin, tape-like extruded web 101 that has been helically wrapped around the rotating mandrel 300. The relatively thick reinforcing coils 402 are components of a helically extending uniform diameter spiral of reinforcement that is formed as the relatively thick extruded bead 201 is helically wrapped around the rotating mandrel 300.

As can be seen in FIG. 4, when the relatively thin extruded web 101 is wrapped around the rotating mandrel 300 in a helical manner, what is formed is a continuously extending spiral that gives the newly-formed hose 400 a thread-like exterior appearance that also can be seen in FIGS. 1 and 2. As FIG. 4 shows, the slanted reaches 405 which are segments of the web-defined spiral have opposed edge regions 406, 407. A leading edge region 407 of the web-defined wall 405 is laid atop a relatively flat, outermost surface of one of the reinforcing coils 402. From the leading edge region 407, the web-defined wall material 405 slants downwardly so that a trailing edge region 406 of the web-defined wall 405 engages the mandrel 300 where the trailing edge region 406 is positioned to underlie and bond to the next-formed reinforcing coil 402 (when a next-to-be-formed reinforcing coil 402 is almost immediately wound onto the turning mandrel 300).

Bonding of the web 101 and the bead 201 normally begins even before the web 101 and the bead 201 are fully fed to the mandrel 300. A completion of the bonding process takes place as the mandrel 300 turns, and as a next bead-defined reinforcing coil is created. In this regard, the coordinated manner in which the web 101 and the bead 201 are presented to and wrapped around the mandrel 300 causes a leading edge region 407 of a web-defined reach 405 to bond to an outer diameter region of a just-formed reinforcing coil 402 at a time before the trailing edge region 406 of the same web-defined reach 405 is bonded to an inner diameter portion of the next-to-be-formed reinforcing coil 402. Between the time when these separate components of the bonding process take place, the mandrel 300 turns to begin formation of the next-to-be-formed reinforcing coil 402.

To be clear, bonding of a leading edge region 407 of each of the web-defined reaches 405 to an outer diameter region of one of the reinforcing coils 402 takes place before a trailing edge region 406 of the same inclined web-defined reach 405 is bonded to a next-to-be-formed reinforcing coil 402. Once a leading edge region 407 is bonded to an outer diameter of one reinforcing coil 402, the mandrel 300 must turn to create a next reinforcing coil 402 which is then laid atop of, and bonded to, the trailing edge region 406 of the same web-defined reach 405.

As can be seen in FIGS. 1-4, the cooperative and coordinated manner in which the freshly extruded web 101 and bead 102 are presented to and wrapped helically about the mandrel 300 (shown in FIGS. 3 and 4) causes the hose 400 to be formed so that it has web and coil formations that extend in an uninterrupted manner, with web reaches 405 ramping up from a trailing edge region 407 adjacent the inner diameter region of one of the reinforcing coils 402 to a leading edge region 406 adjacent the outer diameter region of an adjacent one of the coil formations 402.

The web reaches 405 do not absolutely need to have leading and trailing edge regions 407, 406, respectively, that precisely overlie and precisely underlie the reinforcing coils 402 to which the leading and trailing edge regions 407, 406, respectively, are bonded. Instead, the leading and trailing edge regions 407, 406 of the web reaches 405 can bond to portions of the outer and inner diameter regions that are located quite near to the outermost and innermost surfaces of the reinforcing coils 402. In preferred practice, however, a leading edge 407 of each web reach 405 overlies—(i.e., extends "over" the outer diameter of) the outer diameter of one of the reinforcing coil 402, and a trailing edge 406 of each web reach 405 extends beneath (i.e., extends "under" the inner diameter of) the inner diameter of a next-to-be-formed reinforcing coil 402—which is where the "over and under" designation LhaL has become associated with hoses 400 embodying features of the present invention has had its origin.

Whereas stretch hoses have previously been formed that have thin wall portions that bridge between and connect adjacent pairs of reinforcing coils, these "prior art" hoses have typically utilized web materials that have opposed edges that are 1) both laid "over" the outer diameters of adjacent reinforcing coils, or 2) both laid "under" the inner diameters of adjacent reinforcing coils—which is quite unlike the novel hose construction of the present invention that employs both "over" and "under" bonding of opposed web edges—namely a leading edge 407 that extends "over" the outer diameter of a just-formed reinforcing coil 402, and that extends "under" a next-formed reinforcing coil 402.

This "over and under" bonding of opposite edge regions 407, 406 of connecting web reaches 405 that is utilized by the present invention permits the use of an unusually wide extruded web 101 which provides an unusually lengthy reach of connecting web material 405, and permits the connecting web material 405 to bend or fold radially inwardly at one location, and to bend or fold radially outwardly at a spaced location, so the connecting web reaches 405 take on an S-shaped or a Z-shaped configuration when the hose 400 is axially compressed.

The bend or folds that extend radially inwardly and radially outwardly permit quite an unusually wide web 101 to be used to connect adjacent pairs of the reinforcing coils 402. The lengthy web reaches 405 (that include not only an inwardly extending bend or fold, an outwardly extending bend or fold, and the in-between web-defined material that connects each of the inwardly and outwardly extending bends and folds) permits quite an unusually wide extruded web 101 to be utilized by the resulting hose 400 without causing the hose 400 to exhibit a significantly increased outer diameter, or a significantly diminished inner diameter, when the hose is axially compressed.

The bends or folds that extend radially inwardly and radially outwardly also have the advantage of dividing any needed bending of the web-defined reaches 405 during axial compression of the hose 400. The resulting hose 400 provides an excellent rate of flow for fluid as it passes therethrough (a result of the favorable internal diameter of the hose even when axially compressed), and can fit into relatively tight spaces (a result of the favorable exterior diameter of the hose even when axially compressed).

As has been explained, as the hose 400 is formed it precesses forwardly (as is indicated by the arrow 303 in FIG. 4) along the turning mandrel 300 to discharge from a distal end (not shown) of the mandrel 300. The newly produced hose 400, when discharged, is fully axially extended in the manner depicted in FIGS. 3 and 4. No folds are present in the web reaches 405 which extend between adjacent pairs of the reinforcing coils 402.

Figure 7:
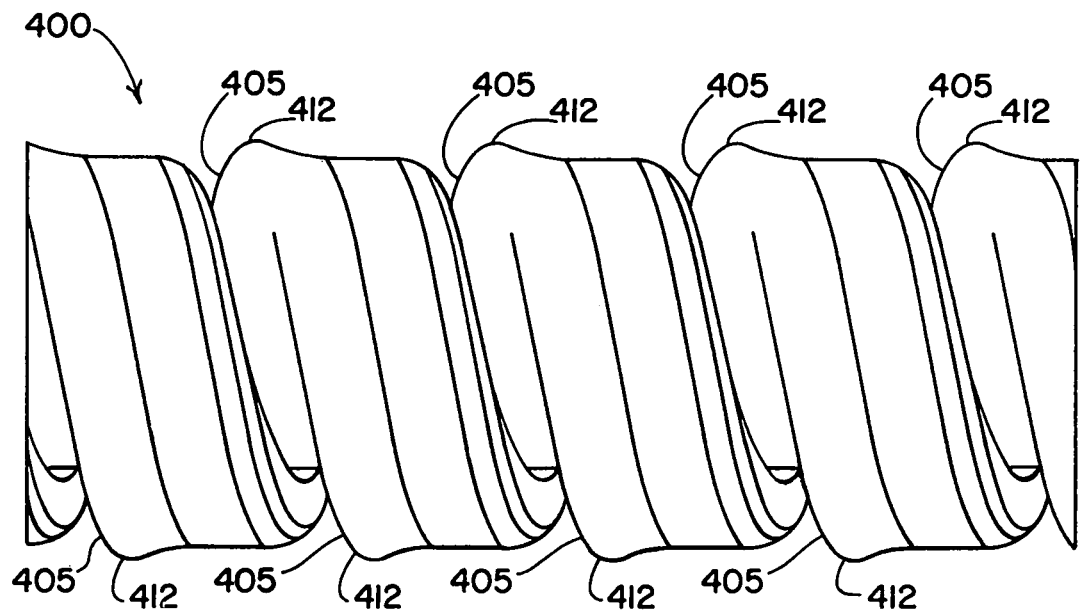
FIG. 7 is a front view of a length of newly formed hose showing how the web-formed walls of the hose bend or fold radially inwardly and outwardly when the length of hose is axially compressed about 30 percent.
Figure 8:
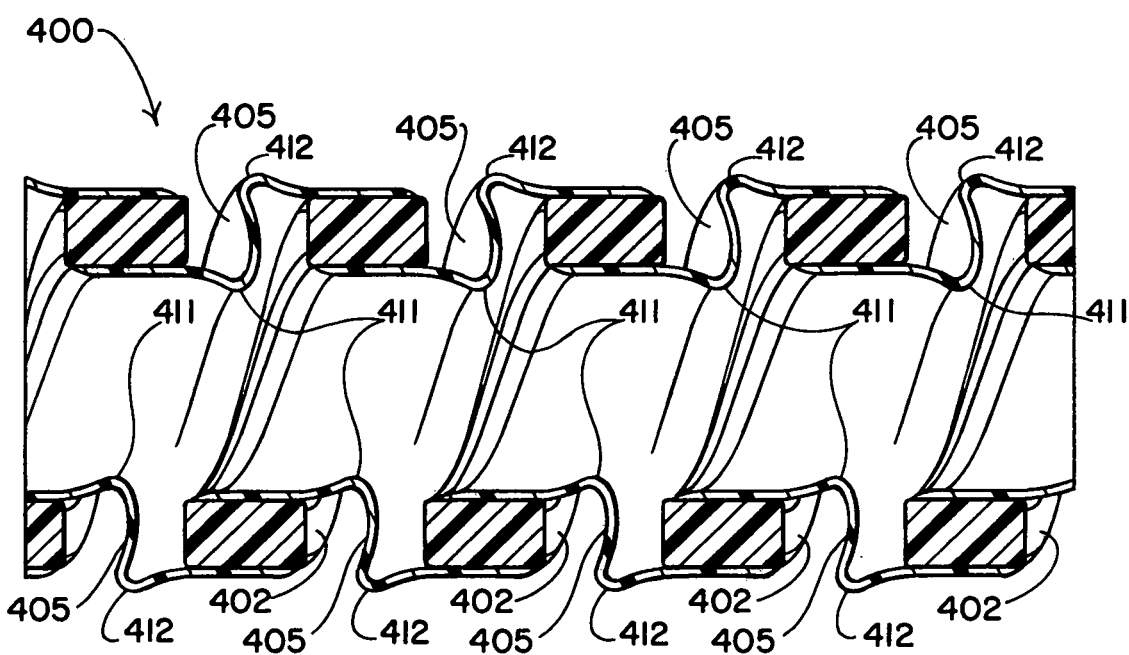
FIG. 8 is a sectional view of the length of partially compressed hose shown in FIG. 7, but with a front half of the hose broken away, and with the rear half of the hose length shown in cross-section.

When the hose 400 is axially compressed, the web reaches 405 begin to bend or fold radially inwardly and radially outwardly, in the manner designated in FIG. 8 by the numerals 411, and in FIGS. 7 and 8 by the numerals 412, respectively. FIGS. 7 and 8 are intended to show the hose 400 axially compressed about 30 percent.

Figure 9:
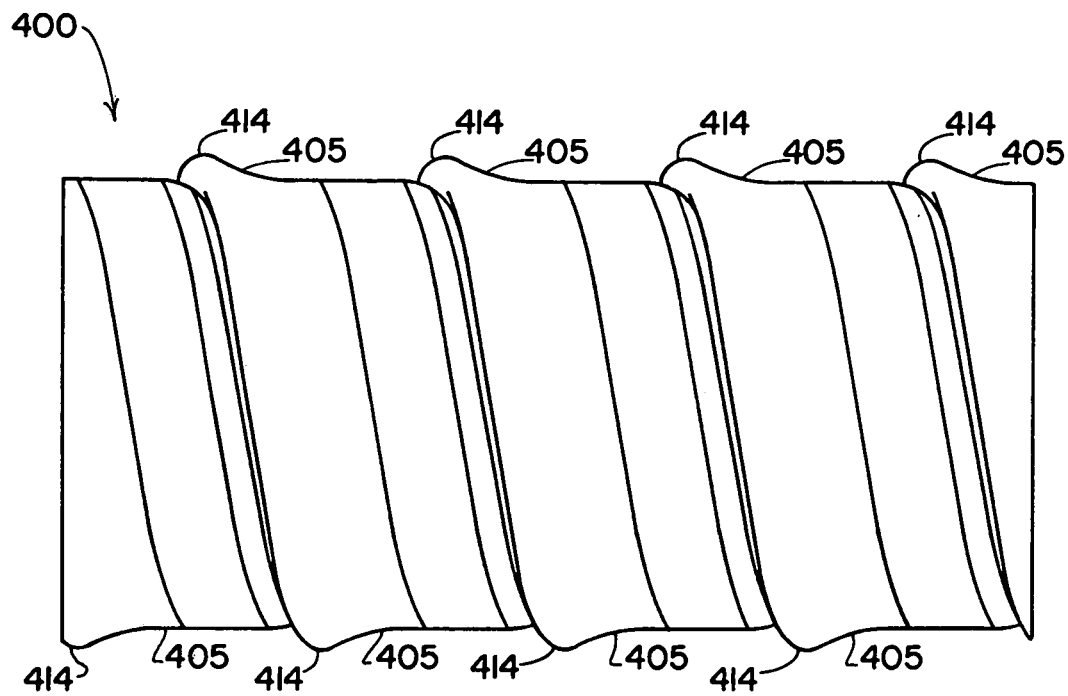
FIG. 9 is a front view of a length of newly formed hose showing how the web-formed walls of the hose bend or fold radially inwardly and outwardly when the length of hose is axially compressed about 60 percent.
Figure 10:
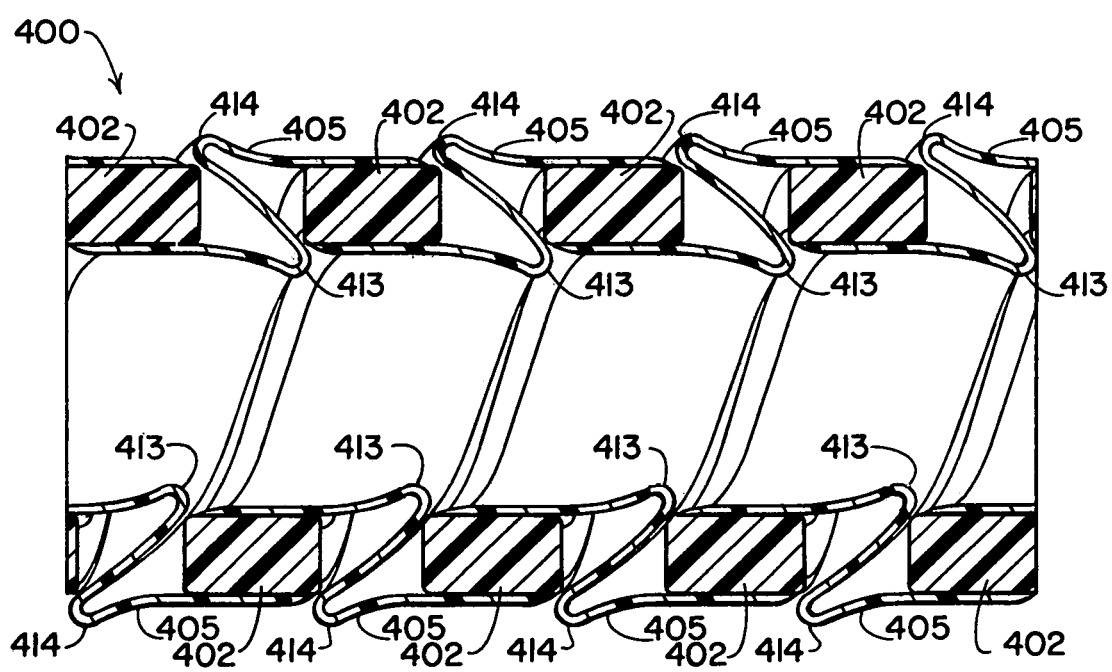
FIG. 10 is a sectional view of the length of more compressed hose shown in FIG. 9, but with a front half of the hose broken away, and with the rear half of the hose length shown in cross-section.

When the hose 400 is more fully axially compressed, the web reaches 405 bend or fold radially inwardly and radially outwardly to a greater extent, in the manner indicated in FIG. 10 by the numerals 413, and in FIGS. 9 and 10 by the numerals 414, respectively. FIGS. 9 and 10 are intended to show the hose 400 axially compressed about 60 percent.

Figure 11:
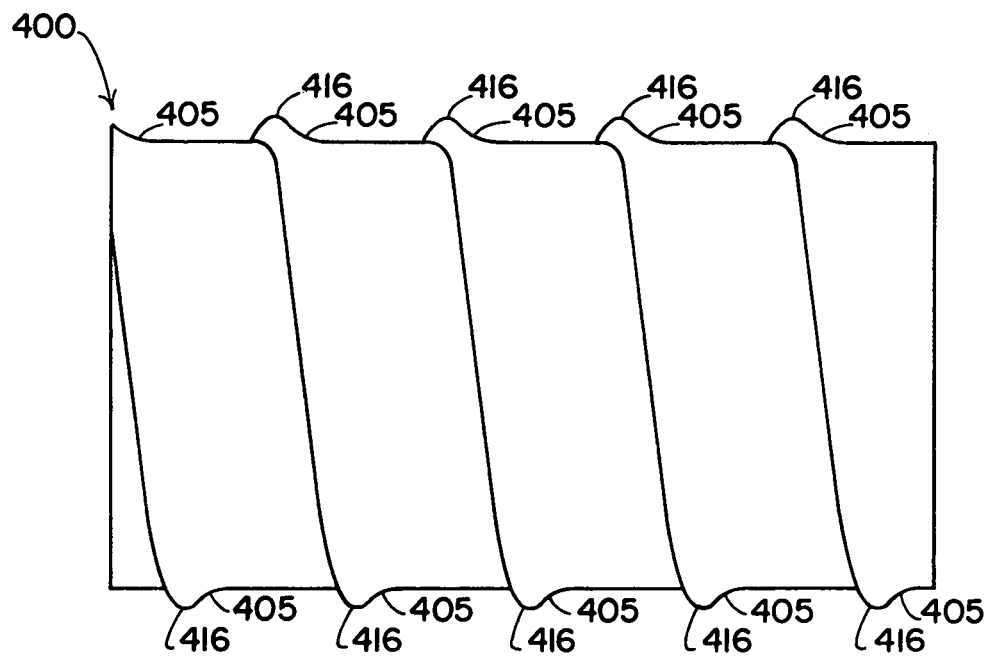
FIG. 11 is a front view of a length of newly formed hose showing how the web-formed walls of the hose bend or fold radially inwardly and outwardly when the length of hose is fully axially compressed.
Figure 12:
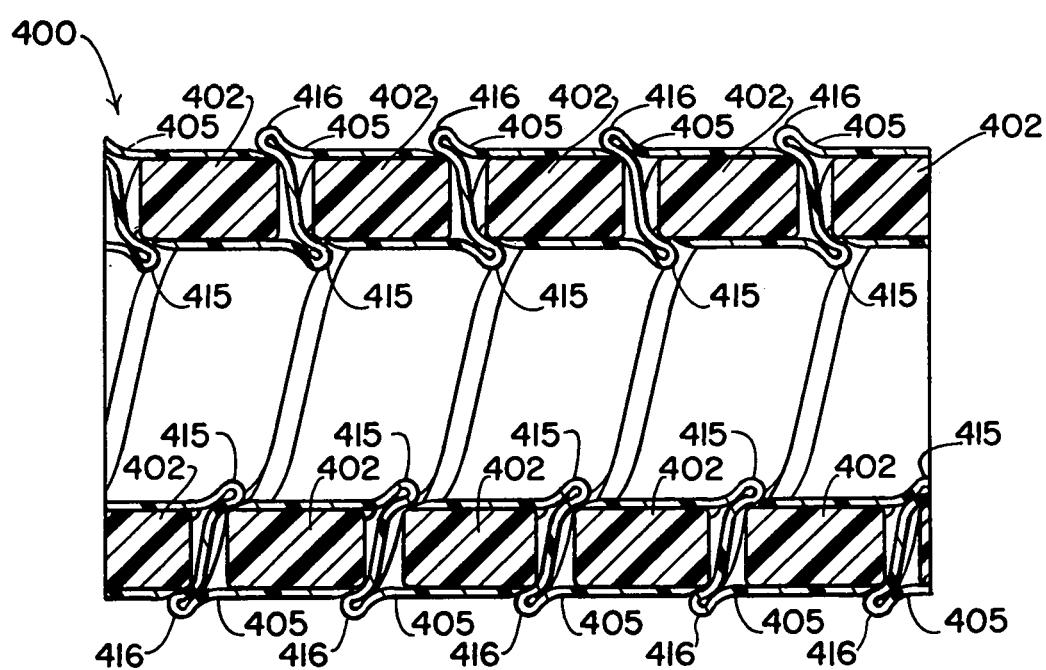
FIG. 12 is a sectional view of the length of fully compressed hose shown in FIG. 11, but with a front half of. the hose broken away, and with the rear half of the hose length shown in cross-section.

When the hose 400 is fully axially compressed, the web reaches 405 bend or fold radially inwardly and radially outwardly to an even greater extent, in the manner indicated in FIG. 12 by the numerals 415, and in FIGS. 11 and 12 by the numerals 416, respectively.

As can be seen in the sequence of views provided by FIGS. 7-8, 9-10 and 11-12, the cooperative and coordinated manner in which the web 201 that forms the web reaches 405 is presented to the rotating mandrel 300 provides a stretch hose 400 that behaves uniquely when retracting, causing each web reach 405 that extends between two adjacent reinforcing coils 402 to assume a generally Z-shape or S-shape—as explained above—with one portion of each web reach 405 folding radially inwardly (as indicated by the numerals 411, 413, 415 in FIGS. 8, 10 and 12, respectively), and with another portion of each web reach 405 folding radially outwardly (as indicated by the numerals 412, 414, 416 in FIGS. 7-8, 9-10 and 11-12, respectively).

The hose 400 can provide a tighter bend radius than typically is exhibited by stretch hoses that employ narrower web widths, as there is only one layer of wall material that is sandwiched between adjacent reinforcing coils 402 of reinforcing material due to the over-and-under arrangement of the leading and trailing edge regions 407, 406, respectively, which cause a center region of the web reaches 405 to extend the full distance from the outer to the inner diameter of the hose 400.

When the hose 400 produced in accord with the preferred method described above also is annealed (as will be described shortly), the resulting hose also has its flexibility greatly enhanced, and its memory advantageously reset, thereby causing the hose to behave quite desirably. The present invention advantageously gives the hose system designer greater flexibility when selecting what hose construction is to be utilized for a particular application. Until now, options have been to use a hose that has an inwardly folding web (but no outwardly folding web) whereby the exterior diameter is minimized so the hose can fit in a confined space, but to sacrifice airflow capacity because interior diameter is diminished—or, to use a hose that has an outwardly folding web (but no inwardly folding web) whereby interior diameter is maximized so the flow rate is not diminished, but to sacrifice the ability of the hose to fit within confined spaces because the exterior diameter of the hose is increased. The hose 400 that embodies features of the present invention that essentially "splits the difference" giving the best of both worlds, and offering unique properties not found in competitive products.

A secondary production step that preferably is performed works with discrete lengths of the newly formed hose 400, which are subjected to axial compression to bring the discrete hose lengths to their minimal axial lengths. With discrete lengths of the hose 400 fully axially compressed, a stress relieving treatment is performed that also has the desirable effect of resetting the "memory" of the lengths of hose 400 to an axially compressed condition of the hose 400.

The effect of stress relief and of the memory of the hose 400 being reset to a minimal axial length of the hose 400 is that, when the hose 400 is stretched and released, the hose 400 will automatically retract toward, and usually completely to, its minimal axial length. Thus, axial extension of the hose 400, followed by release, will result in the hose 400 axially shortening its axial length toward, and usually completely to, the minimal axial length of the hose 400. And, when the hose 400 is both stretched and bent prior to release, this will result in the hose 400 both straightening itself and shortening itself toward a conditional minimal length.

As is described in the above-referenced Annealing System Patent, annealing during axial compression is one way of accomplishing stress relief and memory reset if a discrete length of the hose 400 is annealed while being fully axially compressed to minimal length.

Experiments have also shown that subjecting a fully axially compressed discrete length of the hose 400 to radiation can also accomplish stress relief and memory reset. As other stress relieving and memory resetting techniques are developed, they, too, can be used while discrete lengths of the hose 400 are fully axially compressed.

Figure 13:
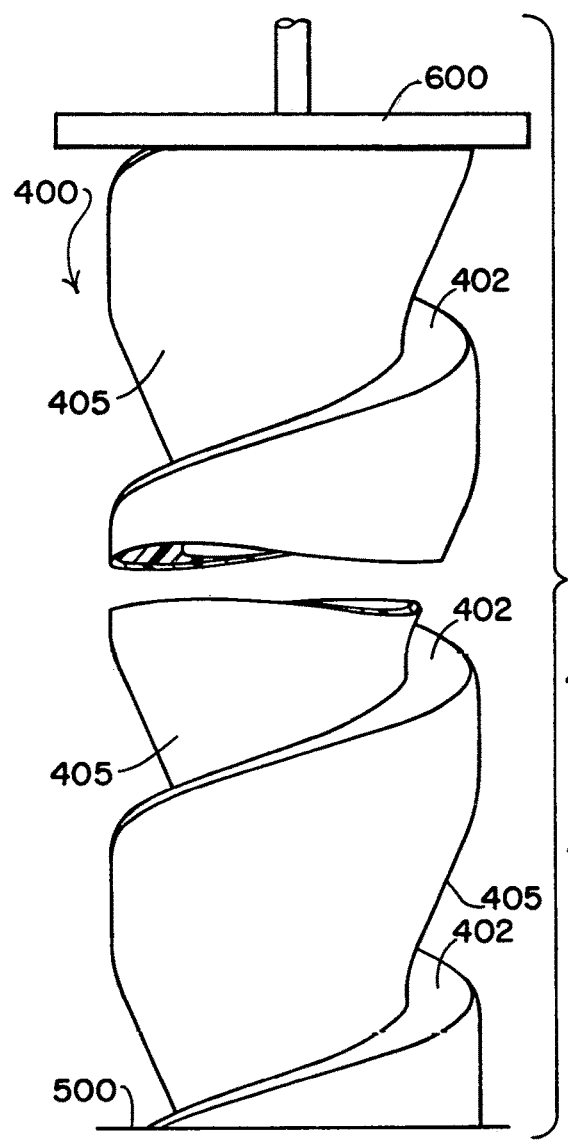
FIG. 13 schematically depicts a discrete but undefined length of fully extended hose positioned atop a flat surface, with an overlying plunger ready to axially compress the discrete hose length; and, FIG. 14 schematically depicts the discrete hose length of FIG. 13 fully axially compressed as the discrete hose length needs to be maintained while being put through a stress-reducing, memory resetting secondary treatment process so that, when the hose is stretched or otherwise extended, then released, the hose will retract toward the depicted minimal axial length—and, when bent while being extended, the hose will straighten as it retracts toward the depicted minimal axial length.
Figure 14:
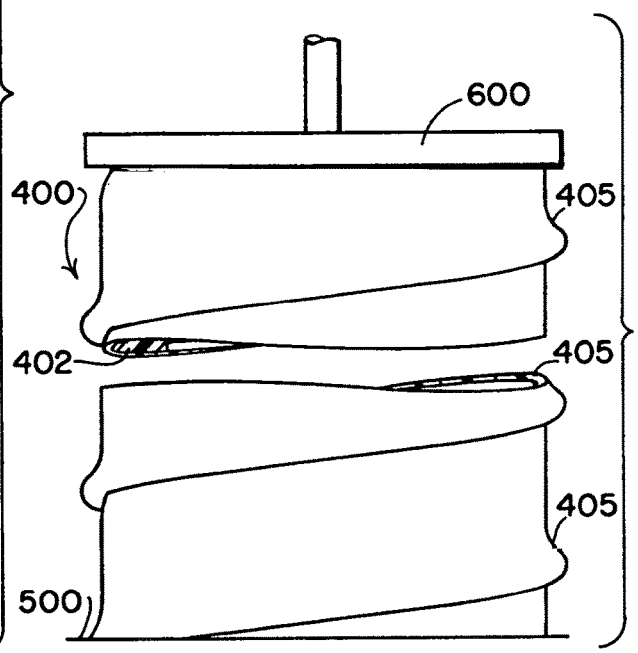

Schematically illustrating mechanical steps of this secondary production step are FIGS. 13 and 14. In FIG. 13, a discrete length of the hose 400 is shown fully extended just as the hose 400 appears in FIGS. 11 and 12 at the conclusion of the production process. In FIG. 13, the hose 400 (which is shown as being of indeterminate length inasmuch as discrete lengths of the hose 400 having substantially any desired length can be treated) is shown with one end region resting atop a substantially flat surface 500. A depressible plunger 600 is shown atop the hose length 400, engaging an opposite end region of the hose length 400.

In FIG. 14, it can be seen that the plunger 600 has been depressed to reduce the axial length of the hose 400 to its fully compressed axial length—such as is shown in FIGS. 11 and 12. With the hose length 400 fully axially compressed in a manner such as is shown in FIG. 14, annealing (or other stress relieving and memory resetting treatment) of the hose length 400 is carried out to relieve internal stress within the newly formed hose 400, and to reset the memory of the axially compressed hose 400.

As the referenced Annealing System Patent explains, annealing during full axial compression of a hose formed from thermoplastic material will reset the memory of the thermoplastic material that forms the hose—so that, after the annealing process (with controlled heating and controlled cooling) has been completed, the hose will return to it minimal axial length when stretched and released, and will straighten and return to its minimal axial length when released after being stretched and bent (or otherwise elastically deformed without being subjected to a further annealing treatment).

Although the invention has been described in its preferred form with a certain degree of particularity, it is understood that the present disclosure of the preferred form has been made only by way of example, and that numerous changes in the details of construction and the combination and arrangement of parts and techniques may be resorted to without departing from the spirit and scope of the invention as hereinafter claimed. It is intended to protect whatever features of patentable novelty that exist in the invention disclosed.

What is claimed is:

1. A method of continuously forming a discrete length of extensible and retractable helically reinforced hose, comprising the steps of:
   a) concurrently continuously extruding both a relatively thin web of thermoplastic material, and a bead of thermoplastic material;
   b) helically wrapping the freshly extruded bead and web around a rotating mandrel in a coordinated manner that continuously forms a hose having a continuously extending helix defined by the bead defining a continuum of axially spaced reinforcing coils, and a sidewall defined by the web that extends in a spiral between and connects each adjacent pair of the reinforcing coils, with the web having two opposed and substantially equally spaced edge regions, with one of the spaced edge regions bonded continuously to a radially outwardly facing bonding surface provided by an outer diameter region of one reinforcing coil of each adjacent pair of reinforcing coils, and with the other of the spaced edge regions bonded continuously to a radially inwardly facing bonding surface provided by an inner diameter region of the other reinforcing coil of each adjacent pair of reinforcing coils such that the two spaced edge regions of the web are continuously radially separated from each other by the continuously extending helix continuously interposed therebetween, and such that the two spaced edge regions of the web are not bonded directly to each other;

c) severing a discrete length of hose from the helically reinforced hose formed as above; and d) stress relieving the discrete length of hose during axial compression of the discrete length of hose to a minimal axial length.

2. The method of claim 1 additionally including the step of resetting the memory of the discrete length of hose during the axial compression to a minimal axial length.

3. The method of claim 1 additionally including the step of annealing the discrete length of hose during the axial compression to a minimal axial length to reset the memory of the thermoplastic material of at least one of the bead and web of the discrete length of hose.

4. The method of claim 1 wherein the web of the discrete length of hose forms a slanted spiral between the spaced edge regions to give the discrete length of hose a thread-like exterior appearance.

5. The method of claim 1 wherein the sidewall of the discrete length of hose has one portion that folds radially outwardly, and another portion that folds radially inwardly when the discrete length of hose is axially compressed.

6. The method of claim 5 wherein the web of the discrete length of hose has a wide width such that, as the discrete length hose is axially extended, the sidewall unfolds and straightens to give the discrete length of hose a relatively long fully axially extended length.

7. The method of claim 5 wherein, when the discrete length of hose is axially compressed, the outwardly folding and the inwardly folding portions of the sidewall cause the sidewall to take on a generally S-shaped or Z-shaped configuration.

8. The method of claim 1 wherein, during formation of the helically reinforced hose, the freshly extruded web and the freshly extruded bead contact and begin to bond before the bead and the web reach the rotating mandrel, with bonding continuing during wrapping of the bead and the web around the rotating mandrel.

9. The method of claim 1 wherein different thermoplastic materials form the web and the bead.

10. The method of claim 9 wherein a harder, somewhat stiffer thermoplastic material is extruded to form the bead than is extruded to form the web.

11. The method of claim 1 wherein the outer diameter region of the one reinforcing coil comprises a radially outermost portion of the one reinforcing coil, and the inner diameter region of the other reinforcing coil comprises a radially innermost portion of the other reinforcing coil.

12. A method of continuously forming a discrete length of axially extensible and retractable hose, comprising the steps of:

a) continuously forming an axially extending helix with axially spaced reinforcing coils from extruded thermoplastic material having a uniform cross-section along its length;

b) continuously bridging between an adjacent pair of the reinforcing coils with a continuous web of extruded thermoplastic material of substantially uniform width and relatively thin cross-section to form a continuous, helically extending sidewall of a hose, with the web having one of two opposite edge regions bonded continuously to a relatively flat outer bonding surface of a radially outwardly located portion of one of the adjacent pair of reinforcing coils, and with the web having the other of the two opposite edge regions bonded continuously to a relatively flat inner bonding surface of a radially inwardly located portion of the other of the adjacent pair of reinforcing coils such that the two opposite edge regions of the web are continuously radially separated from each other by the helix continuously interposed therebetween, and such that the two opposite edge regions of the web are not bonded directly to each other; and c) stress relieving a discrete length of hose that is severed from the axially extensible and retractable hose formed as above during axial compression of the discrete length of hose to a minimal axial length.

13. The method of claim 12 additionally including the step of annealing the discrete length of hose during the axial compression to a minimal axial length to reset the memory of the discrete length of hose to a condition of minimal axial length.

14. The method of claim 12 additionally including the step of annealing the discrete length of hose during the axial compression to a minimal axial length to reset the memory of at least one thermoplastic material forming the discrete length of hose.

15. The method of claim 12 wherein, when the discrete length of hose is axially compressed, one portion of the web extends radially outwardly at a location relatively near to the one of the two opposite edge regions, and another portion of the web extends radially inwardly at a location relatively near to the other of the two opposite edge regions.

16. The method of claim 12 wherein, when the discrete length of hose is axially compressed, one of two spaced portions of the sidewall bends and folds generally radially outwardly, and the other of the two spaced portions of the sidewall bends and folds generally radially inwardly.

17. The method of claim 16 wherein, when the discrete length of hose is axially compressed, the outwardly folding and the inwardly folding spaced portions of the sidewall cause the sidewall to take on a generally S-shaped or Z-shaped configuration.

18. The method of claim 12 wherein the relatively flat outer bonding surface comprises a radially outermost-located surface of the one of the adjacent pair of reinforcing coils, and the relatively flat inner bonding surface comprises a radially innermost-located surface of the other of the adjacent pair of reinforcing coils.

19. The method of claim 12 wherein the discrete length of hose has a thread-like exterior appearance dominated by the web extending in an inclined spiral as it bridges from the outer bonding surface to the inner bonding surface.

20. The method of claim 19 wherein the web of the discrete length of hose has one portion that bends and folds radially outwardly, and another portion that bends and folds radially inwardly when the hose is axially compressed.

21. The method of claim 12 wherein different thermoplastic materials form the web and the helix.

22. The method of claim 21 wherein a harder, somewhat stiffer thermoplastic material is extruded to form the helix than is extruded to form the web.

* * * * *